US012653506B2

(12) United States Patent　　(10) Patent No.:　US 12,653,506 B2
Guo et al.　　　　　　　　　　 (45) **Date of Patent:　*Jun. 16, 2026**

(54) ULTRASOUND BEAMFORMING METHOD AND DEVICE

(71) Applicant: SHENZHEN MINDRAY BIO-MEDICAL ELECTRONICS CO., LTD., Shenzhen (CN)

(72) Inventors: Chongchong Guo, Shenzhen (CN); Jing Liu, Shenzhen (CN); Bo Yang, Shenzhen (CN); Lei Li, Shenzhen (CN); Xuedong Liu, Shenzhen (CN); Muqing Lin, Shenzhen (CN); Qiang Liu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/795,608

(22) Filed: Aug. 6, 2024

(65) Prior Publication Data

US 2024/0393444 A1　　Nov. 28, 2024

Related U.S. Application Data

(63) Continuation of application No. 17/706,490, filed on Mar. 28, 2022, now Pat. No. 12,085,679.

(30) Foreign Application Priority Data

Mar. 25, 2022　(CN) .......................... 202210306948.4

(51) Int. Cl.
　*G01S 7/52*　　　　(2006.01)
　*A61B 8/00*　　　　(2006.01)
　(Continued)

(52) U.S. Cl.
　CPC .............. *A61B 8/5207* (2013.01); *A61B 8/14* (2013.01); *A61B 8/463* (2013.01); *A61B 8/465* (2013.01);
　(Continued)

(58) Field of Classification Search
　CPC ......... A61B 8/5207; A61B 8/14; A61B 8/463; A61B 8/465; A61B 8/469; A61B 8/5238;
　(Continued)

(56) References Cited

U.S. PATENT DOCUMENTS 6,643,406　B1 *　11/2003　Hajjahmad ........ H03H 17/0211
　　　　　　　　　　　　　　　　　　　382/240
9,314,225　B2 *　4/2016　Steen ................... A61B 8/5207
　(Continued)

FOREIGN PATENT DOCUMENTS

CN　　102956030　A　*　3/2013　............... G06T 7/33
CN　　113077394　A　*　7/2021　........... A61B 8/5215
　(Continued)

OTHER PUBLICATIONS

Non-Final Office Action dated Jul. 14, 2023, issued in related U.S. Appl. No. 17/706,490 (43 pages).

*Primary Examiner* — Kaitlyn E Sebastian
(74) *Attorney, Agent, or Firm* — Sheppard Mullin Richter & Hampton LLP

(57)　　　　　　ABSTRACT

Embodiments of the disclosure provide an ultrasound beamforming method and device. The method includes: obtaining channel data of a target tissue; and processing the channel data using at least two different ultrasound beamforming methods to obtain image data of the target tissue corresponding to the different ultrasound beamforming methods, where the at least two different ultrasound beamforming methods are different in at least one of principle, step, and parameter.

19 Claims, 16 Drawing Sheets

(51) Int. Cl.

| | |
|---|---|
| *A61B 8/08* | (2006.01) |
| *A61B 8/14* | (2006.01) |
| *G01S 15/89* | (2006.01) |
| *G06T 5/00* | (2024.01) |
| *G06T 5/50* | (2006.01) |

(52) U.S. Cl.
CPC ............ *A61B 8/469* (2013.01); *A61B 8/5238* (2013.01); *G01S 7/5209* (2013.01); *G01S 15/8977* (2013.01); *G06T 5/50* (2013.01); *G06T 2207/10132* (2013.01); *G06T 2207/20221* (2013.01)

(58) Field of Classification Search
CPC ....... A61B 8/48; A61B 8/5253; G01S 7/5209; G01S 15/8977; G01S 7/52046; G01S 7/52084; G01S 15/8915; G06T 5/50; G06T 2207/10132; G06T 2207/20221
See application file for complete search history.

(56) References Cited

U.S. PATENT DOCUMENTS

| | | | | |
|---|---|---|---|---|
| 12,085,679 | B2 * | 9/2024 | Guo .................... | G01S 7/52046 |
| 2005/0238253 | A1 * | 10/2005 | Behrenbruch ............ | G06T 7/33 |
| | | | | 382/128 |
| 2021/0132223 | A1 * | 5/2021 | Hennersperger .... | G01S 7/52049 |
| 2021/0330289 | A1 * | 10/2021 | Mwikirize .......... | A61B 8/0841 |

FOREIGN PATENT DOCUMENTS

| | | | | |
|---|---|---|---|---|
| JP | 2021186430 A | * | 12/2021 | |
| WO | WO-2018214063 A1 | * | 11/2018 | ............ G06T 15/20 |

* cited by examiner

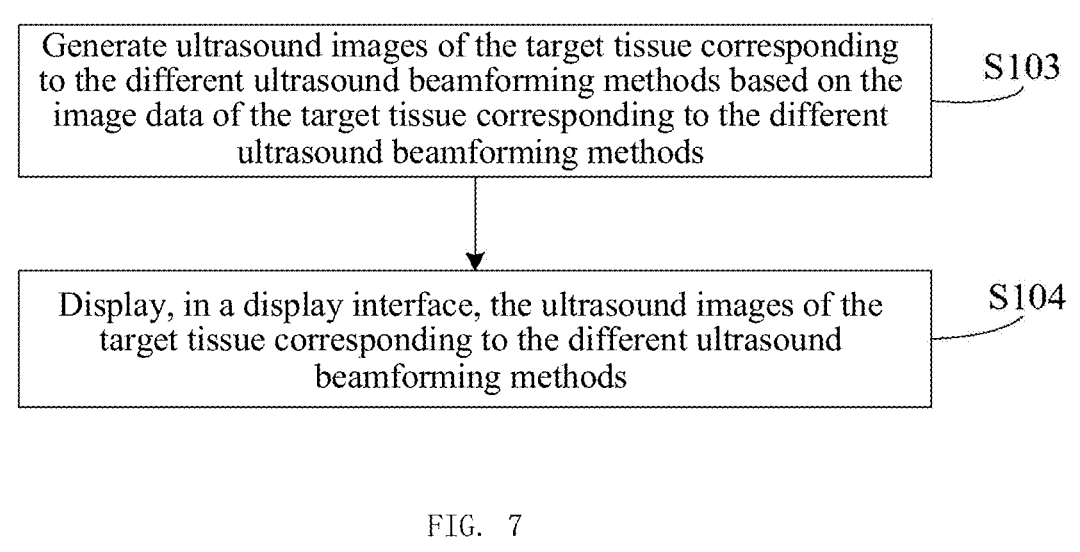

Generate ultrasound images of the target tissue corresponding to the different ultrasound beamforming methods based on the image data of the target tissue corresponding to the different ultrasound beamforming methods          S103

Display, in a display interface, the ultrasound images of the target tissue corresponding to the different ultrasound beamforming methods          S104

FIG. 7

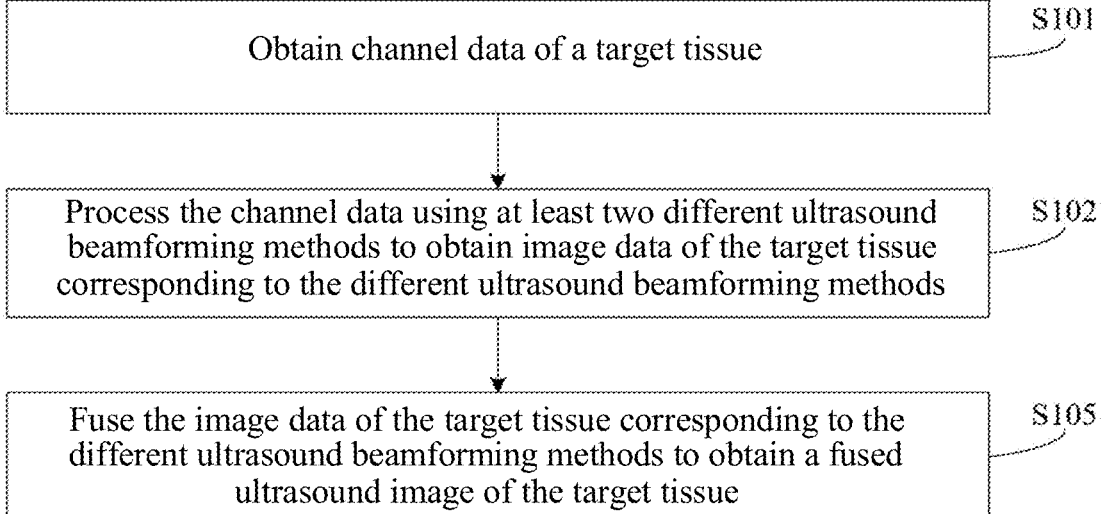

Obtain channel data of a target tissue                                    S101

Process the channel data using at least two different ultrasound beamforming methods to obtain image data of the target tissue corresponding to the different ultrasound beamforming methods        S102

Fuse the image data of the target tissue corresponding to the different ultrasound beamforming methods to obtain a fused ultrasound image of the target tissue        S105

FIG. 8

Please select ultrasound beamforming method

| ☑ | Ultrasound beamforming method A |
| ☐ | Ultrasound beamforming method B |
| ☑ | Ultrasound beamforming method C |
| ☑ | Ultrasound beamforming method D |
| ☐ | Ultrasound beamforming method E |
| ☑ | Ultrasound beamforming method F |
| ☐ | Ultrasound beamforming method G |

( OK )          ( Cancel )

FIG. 9

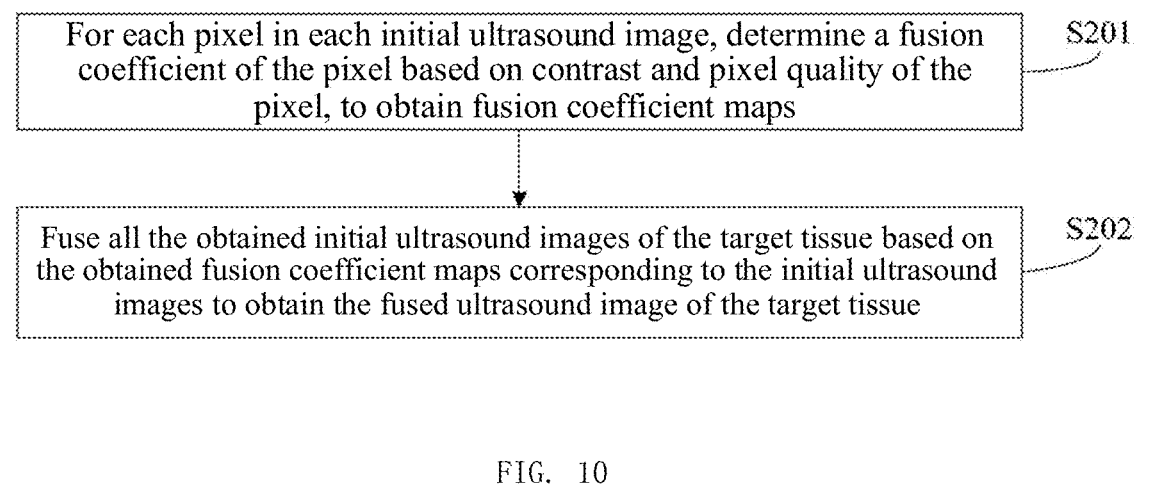

For each pixel in each initial ultrasound image, determine a fusion coefficient of the pixel based on contrast and pixel quality of the pixel, to obtain fusion coefficient maps     S201

Fuse all the obtained initial ultrasound images of the target tissue based on the obtained fusion coefficient maps corresponding to the initial ultrasound images to obtain the fused ultrasound image of the target tissue     S202

FIG. 10

Perform decomposition on each initial ultrasound image using a same image decomposition method, to obtain feature sub-images of the initial ultrasound images          S301

Fuse the obtained feature sub-images to determine the fused ultrasound image of the target tissue          S302

(a)                    (b)                    (c)

ULTRASOUND BEAMFORMING METHOD AND DEVICE

CROSS REFERENCE TO RELATED APPLICATIONS

This application is a continuation of U.S. patent application Ser. No. 17/706,490, filed on Mar. 28, 2022, which is based on and claims priority to and benefits of Chinese Patent Application No. 202210306948.4, filed on Mar. 25, 2022. The contents of the above-identified applications are incorporated herein by reference in their entirety.

TECHNICAL FIELD

The disclosure relates to medical ultrasound imaging, and specifically to an ultrasound beamforming method and device.

BACKGROUND

Diagnostic ultrasound technology has been widely used in clinical practice due to its advantages of non-invasiveness, low cost, and strong real-time performance. In diagnostic ultrasound, a clinical diagnosis is according to an ultrasound image of a tissue, and therefore quality of the ultrasound image will directly affect accuracy of the diagnosis. Ultrasound beamforming is one of the most critical steps in an ultrasound imaging system. Quality of ultrasound beamforming will directly determine quality of a final ultrasound image. Research on an ultrasound beamforming method is of great significance to ensure accuracy of diagnostic ultrasound.

At present, common ultrasound beamforming methods in the industry include a delay-and-sum (DAS) beamforming method, a minimum variance (MV) beamforming method, a coherence factor (CF) beamforming method, etc. An ultrasound image obtained using the delay-and-sum beamforming method can well display an overall structure of a tissue, but cannot clearly display the boundary of the tissue and tiny lesions. The minimum variance beamforming method can improve a spatial resolution of an ultrasound image, but will make an ultrasound image of a homogeneous tissue less dense. The coherence factor beamforming method can make a structure of a strongly reflective tissue clearer, but may cause a failure to display an ultrasound image of a weakly reflective tissue.

In conclusion, the existing ultrasound beamforming methods have some limitations and need to be further improved.

SUMMARY

Embodiments of the disclosure provide an ultrasound beamforming method and device, to improve an existing ultrasound beamforming method and improve quality of an ultrasound image.

In an embodiment, an ultrasound beamforming method is provided, including:

obtaining channel data from echoes returned from a target tissue; and performing at least two beamforming processes on the channel data using at least two different ultrasound beamforming methods to obtain at least two image data frames of the target tissue corresponding to the at least two different ultrasound beamforming methods, wherein, the at least two beamforming processes are performed on the same channel data and each ultrasound beamforming method correspondingly obtains one image data frame, and the at least two different ultrasound beamforming methods are different in at least one of principle, step, and parameter.

In an embodiment, the method further includes:

fusing the at least two image data frames to obtain a fused ultrasound image of the target tissue.

In an embodiment, the method further includes:

respectively generating ultrasound images of the target tissue corresponding to the at least two different ultrasound beamforming methods according to the at least two image data frames; and displaying the ultrasound images of the target tissue corresponding to the at least two different ultrasound beamforming methods.

In an embodiment, before processing the channel data using at least two different ultrasound beamforming methods, the method further includes:

displaying a plurality of ultrasound beamforming methods in the form of text or icons in a display interface for a user to select, and determining the at least two different ultrasound beamforming methods according to the user's selection operation; or obtaining a type of the target tissue and determining the at least two different ultrasound beamforming methods according to the type of the target tissue and a pre-established mapping relationship between a type of tissue and an ultrasound beamforming method.

In an embodiment, fusing the at least two image data frames includes:

determining fusion coefficients corresponding to the at least two different ultrasound beamforming methods according to an application scenario, where the application scenario is determined according to one or more of a probe type, a scanning mode, a frequency of probe, and a scanning depth; and fusing the at least two image data frames of the target tissue using the fusion coefficients.

In one embodiment, fusing the at least two image data frames of the target tissue to obtain a fused ultrasound image of the target tissue includes:

respectively generating, according to the at least two image data frames, at least two initial ultrasound images of the target tissue corresponding to the at least two ultrasound beamforming methods; and fusing the at least two initial ultrasound images according to pixel values or according to image characteristic to obtain the fused ultrasound image of the target tissue.

In an embodiment, fusing the at least two initial ultrasound images according to pixel values to obtain the fused ultrasound image of the target tissue includes:

for each pixel in each initial ultrasound image, determining a fusion coefficient of the pixel according to contrast and pixel quality of the pixel, to obtain fusion coefficient maps corresponding to the at least two initial ultrasound images, where the contrast is positively correlated with a pixel value change amount of the pixel relative to a neighboring pixel, the pixel quality is negatively correlated with a difference between a pixel value of the pixel and a pixel median value, and the fusion coefficient is positively correlated with each of the contrast and the pixel quality; and fusing the at least two obtained initial ultrasound images of the target tissue according to the obtained fusion coefficient maps corresponding to the at least two initial ultrasound images to obtain the fused ultrasound image of the target tissue.

3

In an embodiment, fusing the obtained at least two initial ultrasound images of the target tissue according to the obtained fusion coefficient maps corresponding to the at least two initial ultrasound images includes:

calculating a sum of products of pixel values at a position of pixel in the at least two initial ultrasound images and corresponding fusion coefficients to obtain a pixel value at the position of pixel in the fused ultrasound image.

In an embodiment, fusing the obtained at least two initial ultrasound images of the target tissue according to the obtained fusion coefficient maps corresponding to the at least two initial ultrasound images includes:

performing multi-scale decomposition on each initial ultrasound image and its corresponding fusion coefficient map to obtain ultrasound sub-images and their corresponding fusion coefficient sub-maps at multiple scales;

fusing all ultrasound sub-images at each scale according to their corresponding fusion coefficient sub-maps to obtain fused ultrasound sub-images at the multiple scales; and reconstructing the fused ultrasound sub-images at the multiple scales to obtain the fused ultrasound image.

In an embodiment, performing multi-scale decomposition on each initial ultrasound image and its corresponding fusion coefficient map includes:

performing Laplacian pyramid decomposition on each initial ultrasound image; and performing Gaussian pyramid decomposition on the fusion coefficient map corresponding to each initial ultrasound image.

In an embodiment, fusing the at least two initial ultrasound images according to image characteristic to obtain the fused ultrasound image of the target tissue includes:

performing decomposition on each initial ultrasound image using a same image decomposition method, to obtain multiple characteristic sub-images of the initial ultrasound images; and fusing the obtained characteristic sub-images to obtain the fused ultrasound image of the target tissue.

In an embodiment, performing decomposition on each initial ultrasound image using a same image decomposition method, to obtain characteristic sub-images of the initial ultrasound images includes:

performing singular value decomposition on each initial ultrasound image to obtain a left singular matrix, a singular value matrix, and a right singular matrix of each of the initial ultrasound images, where the singular value matrix includes a singular value of the initial ultrasound image, the left singular matrix includes a left singular vector corresponding to the singular value in the singular value matrix, and the right singular matrix includes a right singular vector corresponding to the singular value in the singular value matrix; and determining a characteristic sub-image corresponding to the singular value according to the singular value and its corresponding left singular vector and right singular vector to obtain the characteristic sub-images of the initial ultrasound images, where amplitude or energy of the singular value is greater than a preset threshold.

In an embodiment, fusing the obtained multiple characteristic sub-images to obtain the fused ultrasound image of the target tissue includes:

determining a fusion coefficient of the characteristic sub-image corresponding to the singular value according to the amplitude or energy of the singular value; and

performing weighted fusion on the obtained characteristic sub-images according to the fusion coefficient to obtain the fused ultrasound image of the target tissue.

In an embodiment, performing decomposition on each initial ultrasound image using a same image decomposition method, to obtain characteristic sub-images of the initial ultrasound images includes:

performing wavelet decomposition on each initial ultrasound image using a same wavelet base and decomposition level, and determining a characteristic sub-image for representing an overall structural feature, a characteristic sub-image for representing a local detail feature in a horizontal direction, a characteristic sub-image for representing a local detail feature in a vertical direction, and a characteristic sub-image for representing a local detail feature in a diagonal direction at each decomposition level, to obtain the characteristic sub-images of the initial ultrasound images.

In an embodiment, fusing the obtained characteristic sub-images to obtain the fused ultrasound image of the target tissue includes:

fusing, according to fusion coefficients, characteristic sub-images located at a same decomposition level and used for representing a same type of feature, to obtain a fused characteristic sub-image at each decomposition level, where the fusion coefficient is a preset fusion coefficient or is determined according to amplitude of the characteristic sub-image; and performing inverse wavelet transform on fused characteristic sub-images at all decomposition levels to determine the fused ultrasound image of the target tissue.

In an embodiment, performing decomposition on each initial ultrasound image using a same image decomposition method, to obtain characteristic sub-images of the initial ultrasound images includes:

decomposing each initial ultrasound image using a same empirical mode decomposition method to obtain a preset quantity of detail characteristic sub-images for representing image detail information at different scales and one structural characteristic sub-image containing image brightness information, so as to obtain the characteristic sub-images of the initial ultrasound images, wherein the detail characteristic sub-image is determined according to an intrinsic mode function component, and the structural characteristic sub-image is determined according to a decomposition residual.

In an embodiment, fusing the obtained multiple characteristic sub-images to obtain the fused ultrasound image of the target tissue includes:

fusing detail characteristic sub-images at each scale to obtain a fused detail characteristic sub-image at said scale, so as to obtain a preset quantity of fused detail characteristic sub-images;

fusing the obtained structural characteristic sub-images to obtain one fused structural characteristic sub-image; and performing reconstruction according to the preset quantity of fused detail characteristic sub-images and the one fused structural characteristic sub-image, to obtain the fused ultrasound image of the target tissue.

In an embodiment, the at least two different ultrasound beamforming methods may include at least two of a delay-and-sum beamforming method, a minimum variance beamforming method, a coherence factor beamforming method, an incoherent beamforming method and a frequency domain beamforming method.

In an embodiment, an ultrasound beamforming method is provided, which may include:

obtaining channel data from echoes returned from a target tissue; and performing at least two beamforming processes on the channel data using at least two different ultrasound beamforming methods to obtain at least two groups of beamformed data of the target tissue corresponding to the at least two different ultrasound beamforming methods, wherein the at least two different ultrasound beamforming methods are different in at least one of principle, step, and parameter;

fusing the at least two groups of beamformed data corresponding to the at least two different ultrasound beamforming methods to obtain fused beamformed data of the target tissue; and generating an ultrasound image of the target tissue according to the fused beamformed data.

In an embodiment, an ultrasound imaging device is provided, including:

an ultrasonic probe;

a transmitter circuit configured to control the ultrasonic probe to transmit an ultrasound wave to a target tissue;

a receiver circuit configured to control the ultrasonic probe to receive echoes of the transmitted ultrasound wave to obtain channel data of the target tissue;

a display configured to output visual information; and a processor configured to perform:

obtaining the channel data of the target tissue; and performing at least two beamforming processes on the channel data using at least two different ultrasound beamforming methods to obtain at least two image data frames of the target tissue corresponding to the at least two different ultrasound beamforming methods, wherein, the at least two beamforming processes are performed on the same channel data and each ultrasound beamforming method correspondingly obtains one image data frame, and the at least two different ultrasound beamforming methods are different in at least one of principle, step, and parameter.

In an embodiment, a computer-readable storage medium having computer executable instructions stored thereon is provided, where the computer executable instructions, when executed by a processor, are used to implement any one of the foregoing ultrasound beamforming methods.

According to the ultrasound beamforming method and device provided in the embodiments of the disclosure, channel data of a target tissue is obtained; and the channel data is processed using at least two different ultrasound beamforming methods to obtain image data of the target tissue corresponding to the different ultrasound beamforming methods, where the at least two different ultrasound beamforming methods have a difference with respect to at least one of principle, step, and parameter. Same channel data is processed using different ultrasound beamforming methods, so that information about a target tissue contained in the channel data can be fully mined, which helps improve the quality of ultrasound imaging.

BRIEF DESCRIPTION OF THE DRAWINGS

FIG. 7 is a flowchart of an ultrasound beamforming method according to another embodiment of the disclosure;

FIG. 8 is a flowchart of an ultrasound beamforming method according to still another embodiment of the disclosure;

FIG. 9 is a schematic diagram of an interface for selecting ultrasound beamforming methods according to an embodiment of the disclosure;

FIG. 10 is a flowchart of fusing initial ultrasound images according to a pixel value of a pixel according to an embodiment of the disclosure;

DESCRIPTION OF THE PREFERRED EMBODIMENTS

Figure 1:
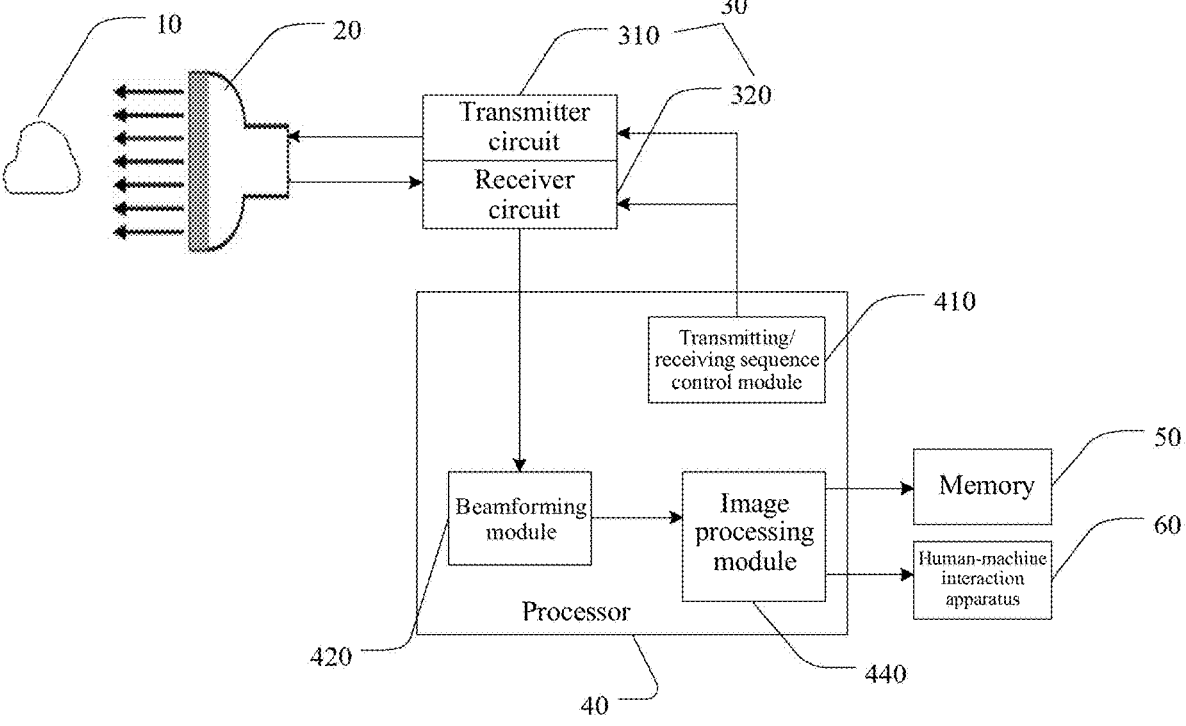
FIG. 1 is a structural block diagram of an ultrasound imaging device according to an embodiment of the disclosure.

The disclosure will be further described in detail below through specific implementations in conjunction with the accompanying drawings. Associated similar element reference numerals are used for similar elements in different implementations. In the following implementations, many details are described such that the disclosure may be better understood. However, it may be effortlessly appreciated by persons skilled in the art that some of the features may be omitted, or may be substituted by other elements, materials, and methods in different cases. In certain cases, some operations involved in the disclosure are not displayed or described in the specification, which is to prevent a core part of the disclosure from being obscured by too much description. Moreover, for persons skilled in the art, the detailed description of the involved operations is not necessary, and the involved operations can be thoroughly understood according to the description in the specification and general technical knowledge in the art.

In addition, the characteristics, operations, or features described in the specification may be combined in any appropriate manner to form various implementations. Meanwhile, the steps or actions in the method description may also be exchanged or adjusted in order in a way that is obvious to persons skilled in the art. Therefore, the various orders in the specification and the accompanying drawings are merely for the purpose of clear description of a certain embodiment and are not meant to be a necessary order unless it is otherwise stated that a certain order must be followed.

The serial numbers themselves for the components herein, for example, "first" and "second", are merely used to distinguish the described objects, and do not have any sequential or technical meaning. Moreover, as used in the disclosure, "connection" or "coupling", unless otherwise stated, includes both direct and indirect connections (couplings).

Ultrasound imaging devices have been widely used due to its advantages of non-invasiveness, low cost, and strong real-time performance. As shown in FIG. 1, an ultrasound imaging device provided in an embodiment of the disclosure may include: an ultrasonic probe 20, a transmitter/receiver circuit 30 (i.e., a transmitter circuit 310 and a receiver circuit 320), a processor 40, a memory 50, and a human-machine interaction apparatus 60. The processor 40 may include a transmitting/receiving sequence control module 410, a beamforming module 420, and an image processing module 440.

The ultrasonic probe 20 includes a transducer (not shown) composed of a plurality of array elements arranged in an array. The plurality of array elements are arranged into a row to form a linear array or into a two-dimensional matrix to form an area array. Alternatively, the plurality of array elements may form a convex array. The array element is configured to transmit an ultrasound beam according to an excitation electrical signal, or convert a received ultrasound beam into an electrical signal. Therefore, each array element may be configured to implement mutual conversion of an electric pulse signal and an ultrasound beam, so as to transmit an ultrasound wave to a target tissue of a subject (a human or an animal), and may be further configured to receive an echo of the ultrasound wave reflected by the target tissue. During ultrasound detection, the transmitter circuit 310 and the receiver circuit 320 may be used to control which array elements are used to transmit an ultrasound beam and which array elements are used to receive an ultrasound beam, or control the array elements to be used to transmit an ultrasound beam or receive an echo of the ultrasound beam in different slots. The array elements participating in transmission of the ultrasound wave can be simultaneously excited by the electrical signal, so as to simultaneously transmit the ultrasound wave; or the array elements participating in transmission of the ultrasound wave may be excited by several electrical signals having a specific time interval, so as to continuously transmit ultrasound waves having a specific time interval.

In this embodiment, a user can move the ultrasonic probe 20 to find an appropriate position and angle to transmit an ultrasound wave to the target tissue 10 and receive an echo of the ultrasound wave returned by the target tissue 10, so as to obtain and output an electrical signal of the echo. The electrical signal of the echo is a channel analog electrical signal formed by using a receiving array element as a channel, and carries amplitude information, frequency information, and time information.

The transmitter circuit 310 is configured to generate a transmitting sequence under control of the transmitting/receiving sequence control module 410. The transmitting sequence is used to control some or all of the plurality of array elements to transmit an ultrasound wave to a biological tissue. Parameters of the transmitting sequence include positions of the array elements, a quantity of the array elements, and transmission parameters of the ultrasound beam (such as amplitude, frequency, times of transmissions, transmission interval, transmission angle, waveform, and focusing position). In some cases, the transmitter circuit 310 is further configured to delay a phase of the transmitted beam, such that different transmitting array elements transmit ultrasound waves at different times, and ultrasound beams transmitted can be focused in a predetermined region of interest. The parameters of the transmitting sequence may vary depending on different working modes, such as B image mode, C image mode, and D image mode (Doppler mode). After an echo signal is received by the receiver circuit 320 and processed by a subsequent module and corresponding algorithm, a B-mode image reflecting an anatomical structure of the target tissue, a C-mode image reflecting the anatomical structure of the target tissue and blood flow information, and a D-mode image reflecting a Doppler spectrum image are generated.

The receiver circuit 320 is configured to receive the electrical signal of the ultrasonic echo from the ultrasonic probe 20 and process the electrical signal of the ultrasonic echo. The receiver circuit 320 may include one or more amplifiers, analog-to-digital converters (ADCs), etc. The amplifier is configured to amplify the received electrical signal of the ultrasonic echo after proper gain compensation. The analog-to-digital converter is configured to sample the analog echo signal at predetermined time intervals, so as to convert the same into a digital signal. The digital echo signal still retains amplitude information, frequency information, and phase information. Data output by the receiver circuit 320 may be output to the beamforming module 420 for processing, or output to the memory 50 for storage.

The processor 40 is configured to be a central controller circuit (CPU), one or more microprocessors, a graphics controller circuit (GPU), or any other electronic component capable of processing input data according to specific logical instructions. The processor may control peripheral electronic components or read and/or store data from and/or to the memory 50 according to input instructions or predetermined instructions, or may process input data by executing a program in the memory 50. For example, one or more processing operations are performed on collected ultrasound data in one or more working modes. The processing operations include, but are not limited to, adjusting or defining the form of an ultrasound wave emitted by the ultrasonic probe 20 and generating various image frames for subsequent display on a display of the human-machine interaction apparatus 60, or adjusting or defining the content and form displayed on the display, or adjusting one or more image display settings (e.g., ultrasound image, interface component, locating a region of interest) displayed on the display.

The beamforming module 420 may be connected to the receiver circuit 320 via a signal, and is configured to perform beamforming on channel data of the target tissue output by the receiver circuit 320, to obtain beamformed ultrasound image data. In this case, the channel data is a radio frequency signal that has not been demodulated, and ultrasound image data output by the beamforming module 420 is also radio frequency data (RF data). The beamforming module 420 may output the radio frequency data to an IQ demodulation module (not shown) for demodulation to obtain baseband data. The IQ demodulation module may output the baseband data to the image processing module 440 of the processor 40 for image processing, or may output the baseband data to the memory 50 for buffering or storage, so that the image processing module 440 reads data from the memory 50 for subsequent image processing. Alternatively, the beamforming module 420 may output the radio frequency data to the memory 50 for buffering or storage, or directly output the radio frequency data to the image processing module 440 of the processor 40 for image processing.

In an optional implementation, alternatively, the IQ demodulation module (not shown) may be located between the beamforming module 420 and the receiver circuit 320. To be specific, the IQ demodulation module may be connected to the receiver circuit 320 via a signal, remove a signal carrier through IQ demodulation to extract tissue structure information contained in the signal, and perform filtering to remove noise. A signal obtained in this case is referred to as a baseband signal. The beamforming module 420 may be connected to the IQ demodulation module via a signal and configured to perform beamforming on channel data of the target tissue output by the IQ demodulation module, to obtain beamformed ultrasound image data. In this case, the channel data is a demodulated baseband signal, and ultrasound image data output by the beamforming module 420 is also baseband data. In addition, the beamforming module 420 may output the baseband data to the memory 50 for buffering or storage, or directly output the baseband data to the image processing module 440 of the processor 40 for image processing.

The channel data processed by the beamforming module 420 may be a radio frequency signal or a demodulated baseband signal.

The beamforming module 420 may perform the above functions by hardware, firmware, or software. For example, the beamforming module 420 may include a central controller circuit (CPU), one or more microprocessors, or any other electronic component capable of processing input data according to specific logical instructions. When implemented by software, the beamforming module 420 may execute instructions stored on a tangible and non-transitory computer-readable medium (e.g., the memory 50) to perform beamforming calculation using any suitable beamforming method.

The image processing module 440 is configured to process the data output by the beamforming module 420 or the data output by the IQ demodulation module (not shown), to generate the ultrasound image of the target tissue. The image processing module 440 may output the obtained ultrasound image of the target tissue to the display of the human-machine interaction apparatus 60 for display.

The memory 50 may be a tangible and non-transitory computer-readable medium, for example, may be a flash memory card, a solid-state memory, a hard disk, etc., for storing data or a program. For example, the memory 50 may be configured to store the collected ultrasound data or an image frame that is generated by the processor 40 but is not immediately displayed; or the memory 50 may store a graphical user interface, one or more default image display settings, and programming instructions for the processor, the beamforming module 420, or the IQ decoding module.

The human-machine interaction apparatus 60 is configured to perform human-machine interaction, that is, receive an input of a user and output visual information. The human-machine interaction apparatus may receive the input of the user using a keyboard, an operation button, a mouse, a trackball, etc., or using a touchscreen integrated with the display. The human-machine apparatus outputs the visual information using the display.

It should be noted that the structure shown in FIG. 1 is only for illustration, and in actual use, more or fewer components/modules than those shown in FIG. 1 may be included, or a configuration different from that shown in FIG. 1 may be used. The components/modules shown in FIG. 1 may be implemented by hardware and/or software. The ultrasound imaging device shown in FIG. 1 may be configured to perform an ultrasound beamforming method provided in any embodiment of the disclosure.

Because an ultrasound wave receiving point in the target tissue has different distances from different receiving array elements, channel data of the same receiving point that is output by the different receiving array elements have a delay difference, which needs to be eliminated through beamforming. The beamforming is of great significance and is a key factor affecting the quality of ultrasound imaging.

Figure 2:
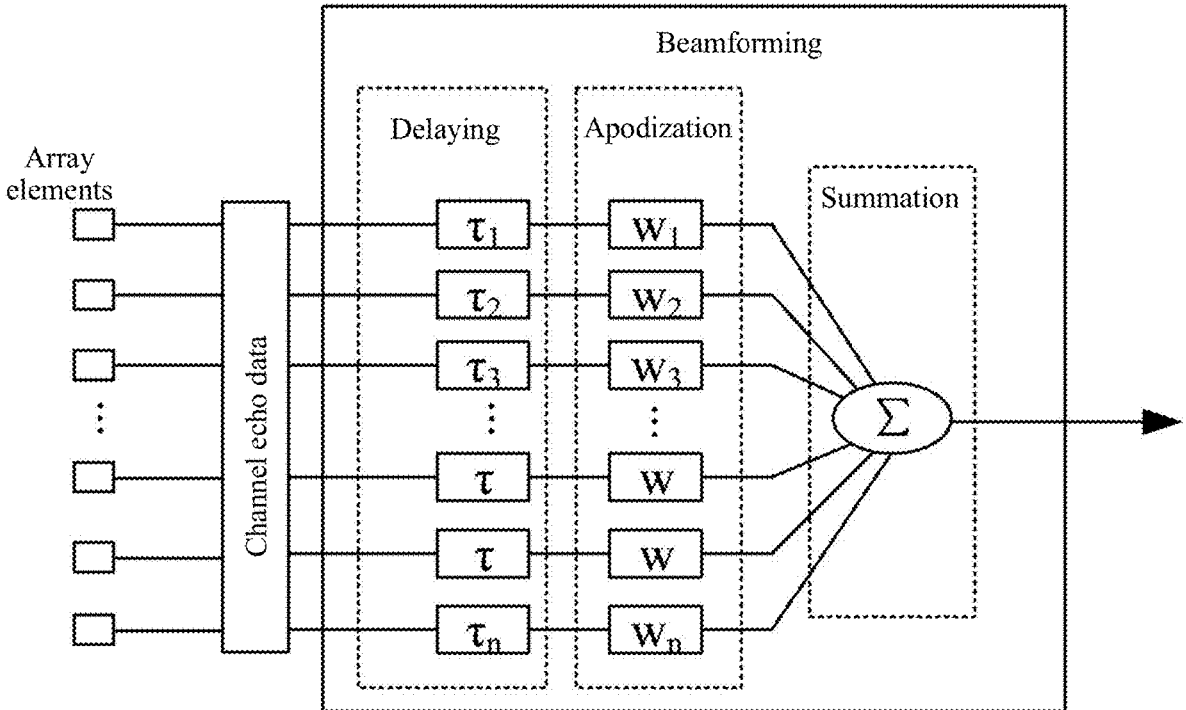
FIG. 2 is a schematic flowchart of a DAS beamforming method.

As shown in FIG. 2, a delay-and-sum (DAS) beamforming method includes three steps: delaying, apodization, and summation. The DAS beamforming method has been widely used in ultrasound imaging devices because of its advantages such as simple implementation principle, easy implementation, and high image robustness. According to the method, the channel data is aligned according to corresponding delay coefficients ($\tau_1$, $\tau_2$, $\tau_3$ . . . ), and then is weighted summed according to corresponding apodization coefficients ($w_1$, $w_2$, $w_3$ . . . ). The delay coefficient and the apodization coefficient are two important parameters for the DAS beamforming method. The delay coefficient may be determined according to a geometric position of an imaging point in an emission sound field and a geometric distance from a position of an array element. The apodization coefficient is usually a set of fixed window functions such as rectangular windows, Hanning windows, Gaussian windows, or semicircular windows.

Figure 3:
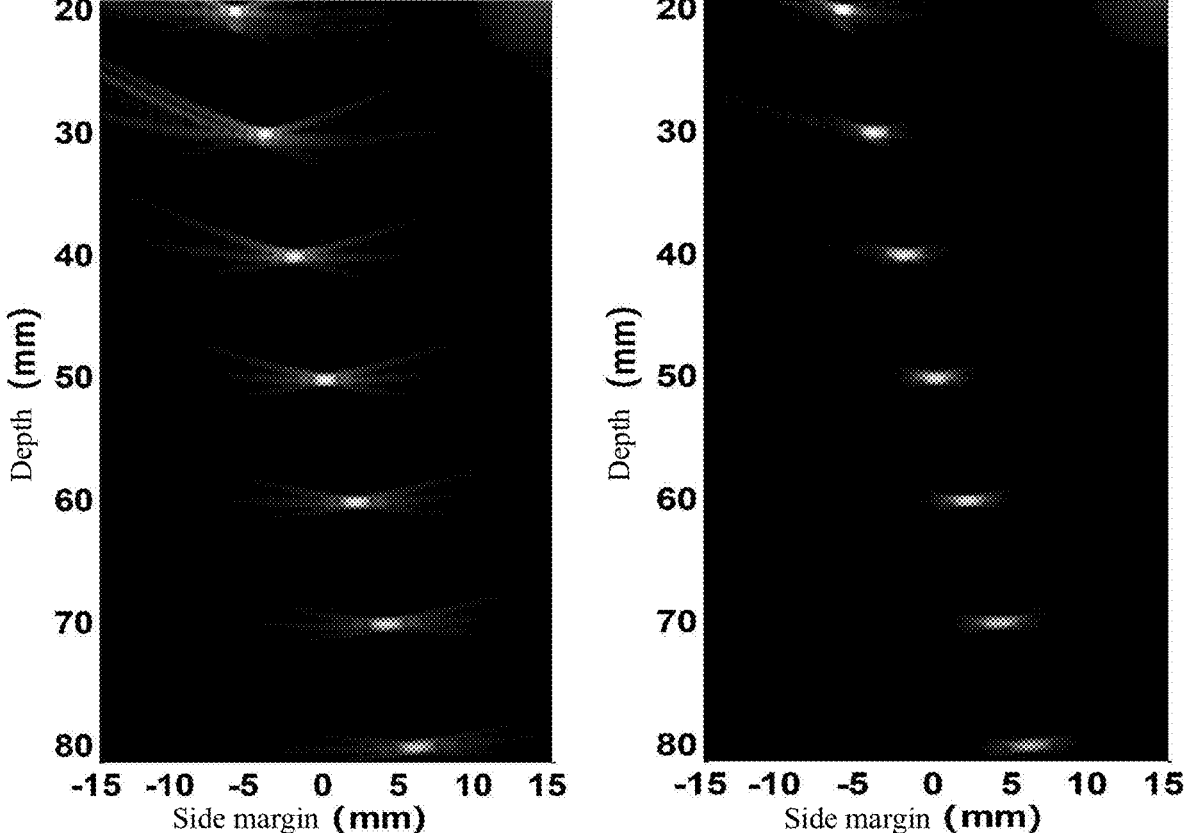
FIG. 3 is a schematic diagram of images corresponding to different window functions in a DAS beamforming method.

Different image effects can be obtained by applying different window functions. As shown in FIG. 3, an image on the left represents an image obtained by applying a rectangular window, and an image on the right represents an image obtained by applying a Gaussian window. A target point corresponding to the rectangular window has a narrow main lobe but a high side lobe, and an image representation features a relatively high spatial resolution, but there is clutter interference. A target point corresponding to the Gaussian window has a wide main lobe but a low side lobe, and an image representation features a poor spatial resolution, but there is less clutter and a low noise level. In practical applications, ultrasound research engineers need to adjust the delay coefficient and the apodization coefficient depending on actual situations, so as to make a choice between images.

It can be seen that an ultrasound image obtained using the DAS beamforming method can well display an overall structure of a tissue, but cannot clearly display the boundary of the tissue and tiny lesions. This is because relevant assumptions applied in the calculation process of the delay coefficient are not completely in line with the actual situations, and also because the apodization coefficient used is fixed and cannot adaptively change depending on characteristics of the ultrasonic echo signal.

In order to improve the quality of ultrasound images, the industry has proposed beamforming methods that can adaptively change depending on the characteristics of the ultrasonic echo signal, such as a minimum variance (MV) beamforming method, a coherence factor (CF) beamforming method, an incoherent beamforming method, a frequency domain beamforming method, and the like.

Figure 4:
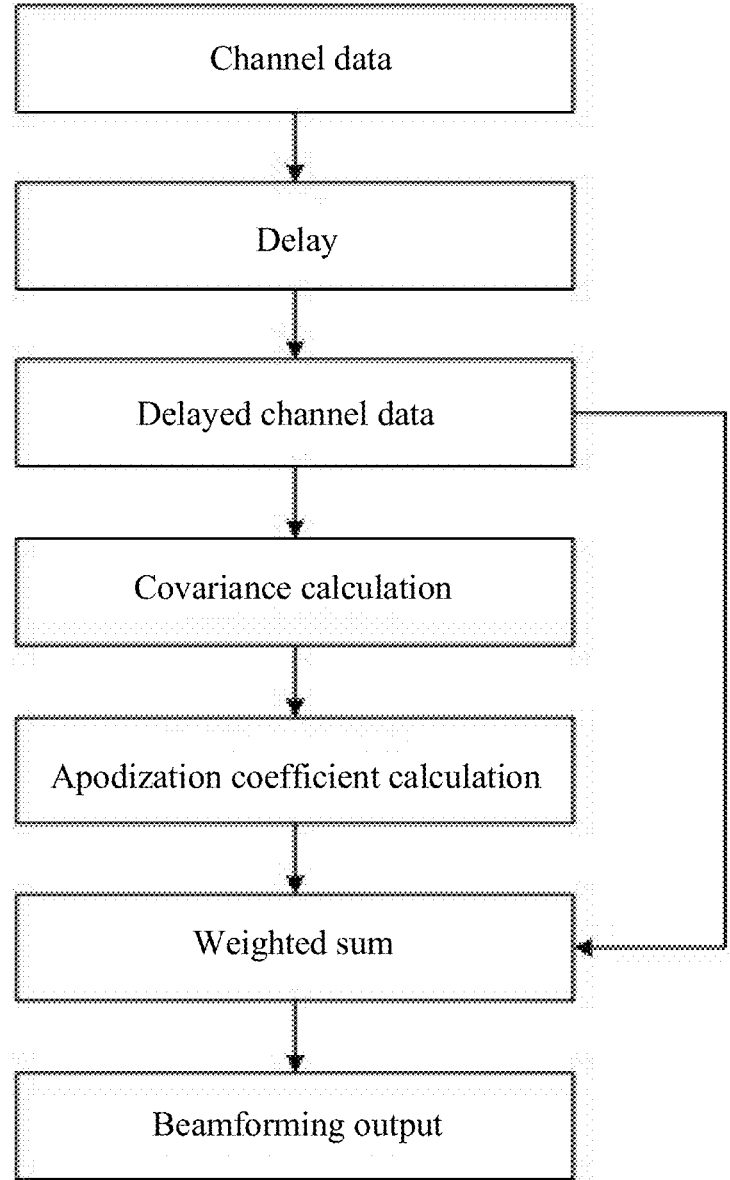
FIG. 4 is a schematic flowchart of a MV beamforming method.

As shown in FIG. 4, in the MV beamforming method, channel data is first delayed; then a covariance matrix for the delayed channel data is calculated, an output with minimized noise and interference is used as an optimization goal, and a set of apodization coefficients are calculated; and a weighted sum of the delayed channel data is calculated according to the obtained apodization coefficients, to obtain a beamforming output. Because an apodization coefficient in the MV beamforming method is adaptively calculated in real time according to the received channel data, the apodization coefficient is not fixed. This method can improve a spatial resolution and a contrast resolution of an ultrasound image, but speckle noise has a large variance, and the image has relatively strong background noise, which will make an ultrasound image of a homogeneous tissue less dense, causing a defect.

Figure 5:
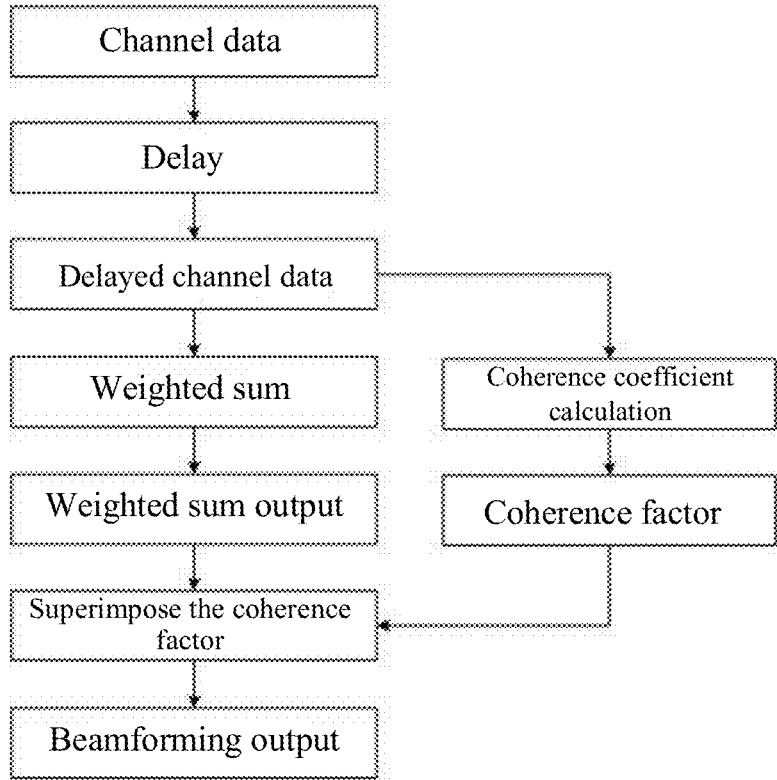
FIG. 5 is a schematic flowchart of a CF beamforming method.

As shown in FIG. 5, in the CF beamforming method, channel data is first delayed to obtain the delayed channel data. According to specific a priori knowledge, different weights are assigned to the delayed channel data, to obtain a weighted summation output. Assuming that an effective signal of the channel data has specific coherence, while a noise signal is incoherent, coherence coefficient calculation is performed according to the coherent signal and the incoherent signal in the delayed channel data to obtain a coherence factor. Then, the obtained coherence factor and a result of the weighted summation output are processed to obtain a beamforming output. The CF beamforming method has a significant effect on a strongly reflective signal, and will make a structure of a strongly reflective tissue clearer and enhance the contrast of the image. However, for a weak signal, a calculated coherence factor coefficient is relatively small, which will further compress the weak signal, causing a failure to display part of an image.

It should be noted that there are many ultrasound beamforming methods applicable to the ultrasound imaging device, which are not described herein one by one.

In conclusion, an ultrasound image obtained using the DAS beamforming method can well display an overall structure of a tissue, but cannot clearly display the boundary of the tissue and tiny lesions. The MV beamforming method can improve a spatial resolution of an ultrasound image, but will make an ultrasound image of a homogeneous tissue less dense. The CF beamforming method can make a structure of a strongly reflective tissue clearer, but may cause a failure to display an ultrasound image of a weakly reflective tissue.

It can be seen that different beamforming methods have different characteristics and each have some advantages and disadvantages. The methods can highlight information of the target tissue in a specific aspect, but cannot replace each other. In order to fully mine information about the target tissue contained in the channel data, the applicant proposes an ultrasound beamforming method, in which same channel data is processed using different ultrasound beamforming methods, so that the information about the target tissue can be obtained from multiple perspectives, which helps improve the quality of ultrasound imaging of the target tissue. The following provides a detailed description by using specific embodiments.

Figure 6:
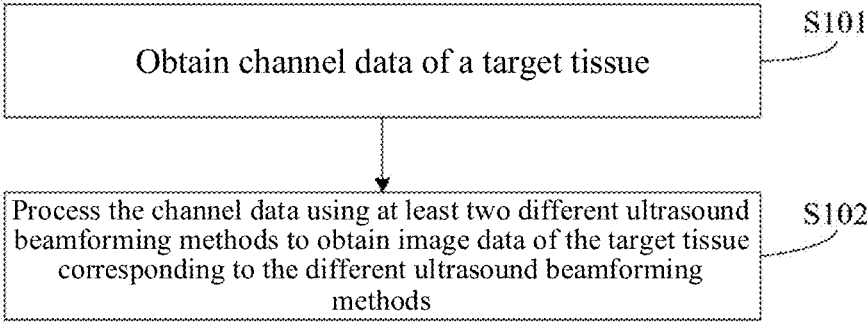
FIG. 6 is a flowchart of an ultrasound beamforming method according to an embodiment of the disclosure.

FIG. 6 is a flowchart of an ultrasound beamforming method according to an embodiment of the disclosure. As shown in FIG. 6, the ultrasound beamforming method provided in this embodiment may include the following steps.

S101: Obtain channel data of a target tissue.

In this embodiment, an ultrasonic probe may be used to transmit an ultrasound wave to the target tissue and receive an ultrasonic echo returned by the target tissue, to obtain the channel data of the target tissue in real time; or the pre-stored channel data of the target tissue may be obtained from a storage device.

It should be noted that the channel data herein may be data corresponding to a channel (corresponding to one or more array elements) of an ultrasound imaging device and not being beamformed. For example, the data may be a radio frequency signal before demodulation or a baseband signal after demodulation, etc.

S102: Process the channel data using at least two different ultrasound beamforming methods to obtain at least two image data frames of the target tissue corresponding to the different ultrasound beamforming methods, where the at least two different ultrasound beamforming methods are difference in at least one of principle, step, and parameter. The at least two different ultrasound beamforming methods may include at least two of a delay-and-sum beamforming method, a minimum variance beamforming method, a coherence factor beamforming method, an incoherent beamforming method and a frequency domain beamforming method, etc.

In this embodiment, after the channel data of the target tissue is obtained, two or more different ultrasound beamforming methods may be used to perform at least two beamforming processes on the same channel data, i.e., the same channel data is beamformed at least twice using at least two different ultrasound beamforming methods, and one image data frame may be obtained from the beamformed data obtained by each ultrasound beamforming method after following processes (here, one image data "frame" refers to a collection of image data obtained by one beamforming process, which may be a complete image frame or a part of a complete image frame). The same channel data is processed, that is, data of the target tissue only needs to be collected once, which can reduce a data collection time and reduce a requirement for data storage space.

In this disclosure, when referring to "different beamforming methods" or "multiple beamforming methods", it means that the beamforming methods are different in at least one of principles, steps and parameters. It may be that the beamforming algorithms (principles) are different. It may also be that the algorithms (principles) are the same, but the steps are different (for example, there is added or removed steps or the order of the steps is changed, etc.) or the parameters used are different, etc. The beamforming methods in these cases shall all be considered as "different" beamforming methods.

In this embodiment, the different ultrasound beamforming methods are ultrasound beamforming methods having a difference with respect to at least one of principle, step, and parameter. Using a first ultrasound beamforming method, a second ultrasound beamforming method, and a third ultrasound beamforming method to process the channel data of the target tissue is taken as an example for description. In an optional implementation, the first ultrasound beamforming method may be a DAS beamforming method, the second ultrasound beamforming method may be an MV beamforming method, and the third ultrasound beamforming method may be a CF beamforming method, that is, ultrasound beamforming methods having different principles are used. In another optional implementation, the first ultrasound beamforming method may be a DAS beamforming method according to a rectangular window, the second ultrasound beamforming method may be a DAS beamforming method according to a Gaussian window, and the third ultrasound beamforming method may be a DAS beamforming method according to a semicircular window, that is, ultrasound beamforming methods having the same principle but different parameters are used. In still another optional implementation, the first ultrasound beamforming method may be a DAS beamforming method; the second ultrasound beamforming method may be a CF beamforming method in which a coherence factor is first calculated, then weighted summation is performed, and finally the coherence factor is superimposed; and the third ultrasound beamforming method may be a CF beamforming method in which weighted summation is first performed, then a coherence factor is calculated, and finally the coherence factor is superimposed. That is, ultrasound beamforming methods having a difference in principle and step are used. It should be noted that the above combinations are only examples and are not limiting. In actual use, at least two different ultrasound beamforming methods may be selected according to specific conditions. Furthermore, in the present disclosure, the ultrasound beamforming method will not be limited to those described above. Any other suitable beamforming method now or in the future may also be used.

It may be understood that the different ultrasound beamforming methods can highlight information about the target tissue from different perspectives. For example, the DAS beamforming method can highlight an overall structure of the target tissue; the MV beamforming method improves a spatial resolution, so that tiny lesions in the target tissue can be highlighted; and the CF beamforming method can make it possible to clearly display a strongly reflective part in the target tissue. Therefore, using the at least two different ultrasound beamforming methods to process the same channel data makes it possible to obtain the information about the target tissue from multiple different perspectives and fully mine information contained in the channel data, which helps improve the quality of ultrasound imaging.

In addition, with the continuous development of computer science and technology, computing power of an ultrasound imaging system is also continuously increased. Using at least two different ultrasound beamforming methods to process the same channel data can also make it possible to fully utilize the computing power of the ultrasound imaging system, avoiding a waste of computing power resources.

In a real-time imaging application scenario, the at least two different ultrasound beamforming methods may be used to process the same channel data in parallel, so as to improve a processing speed and meet the need of real-time imaging.

It should be noted that the ultrasound beamforming methods for processing the channel data in this embodiment include both an existing ultrasound beamforming method in the art and an ultrasound beamforming method that may appear in the art in the future.

According to the ultrasound beamforming method provided in this embodiment, the channel data of the target tissue is first obtained, and then the at least two different ultrasound beamforming methods are used to process the channel data, to obtain at least two image data frame of the target tissue corresponding to the different ultrasound beamforming methods. Using the different ultrasound beamforming methods to process the same channel data makes it possible to obtain the information about the target tissue from different perspectives and fully mine information contained in the channel data, which helps improve the quality of ultrasound imaging.

As shown in FIG. 7, to help the user observe the target tissue from different perspectives, on the basis of the embodiment shown in FIG. 6, the ultrasound beamforming method provided in this embodiment may further include the following steps.

S103: Generate ultrasound images of the target tissue corresponding to the different ultrasound beamforming methods according to the image data of the target tissue corresponding to the different ultrasound beamforming methods.

Using the DAS beamforming method, the MV beamforming method, and the CF beamforming method to process the same channel data of the target tissue is taken as an example for description. First image data of the target tissue may be obtained after processing using the DAS beamforming method, second image data of the target tissue may be obtained after processing using the MV beamforming method, and third image data of the target tissue may be obtained after processing using the CF beamforming method.

The obtained image data may be processed by using an image processing module in a processor of the ultrasound imaging device, to generate a corresponding ultrasound image. For example, a first ultrasound image of the target tissue may be generated according to the first image data, and the first ultrasound image obtained using the DAS beamforming method can well present the overall structure of the target tissue; a second ultrasound image of the target tissue may be generated according to the second image data, and the second ultrasound image obtained using the MV beamforming method has a relatively high spatial resolution and can highlight tiny lesions in the target tissue; and a third ultrasound image of the target tissue may be generated according to the third image data, and the third ultrasound image obtained using the CF beamforming method can more clearly display a strongly reflective part in the target tissue.

S104: Display, in a display interface, the ultrasound images of the target tissue corresponding to the different ultrasound beamforming methods.

Because the ultrasound images of the target tissue corresponding to different ultrasound beamforming methods are generated according to the same channel data, there is no need to register the obtained ultrasound images, and the obtained ultrasound images may be directly displayed in the display interface, so that the target tissue can be presented in such a manner available for comparison. For example, the obtained first ultrasound image, second ultrasound image, and third ultrasound image may be displayed in the display interface in a tiling form. In this case, the user can grasp the overall structure of the target tissue from the first ultrasound image, view the tiny lesions in the target tissue from the second ultrasound image, and observe the strongly reflective part in the target tissue from the third ultrasound image. Displaying the ultrasound images obtained using the different beamforming methods in the display interface makes it possible for the user to observe the target tissue from different perspectives and grasp more information about the target tissue, which facilitates a more comprehensive and accurate grasp of the situation of the target tissue.

It should be noted that in an actual use process, more or fewer ultrasound beamforming methods may be selected as required to generate and display more or fewer ultrasound images. The types and quantity of the used ultrasound beamforming methods and the quantity and display manner of the generated ultrasound images are not limited in this embodiment.

According to the ultrasound beamforming method provided in this embodiment, after the at least two different ultrasound beamforming methods are used to process the same channel data, and the image data of the target tissue corresponding to the different ultrasound beamforming methods are obtained, the ultrasound images of the target tissue corresponding to the different ultrasound beamforming methods are generated according to the image data of the target tissue corresponding to the different ultrasound beamforming methods, and are displayed in the display interface. Displaying the ultrasound images obtained using the different beamforming methods in the display interface makes it possible for the user to observe the target tissue from different perspectives and grasp more information about the target tissue, which facilitates a more comprehensive and accurate grasp of the situation of the target tissue.

As shown in FIG. 8, to facilitate the observation of the target tissue, on the basis of the embodiment shown in FIG. 6, the ultrasound beamforming method provided in this embodiment may further include the following step.

S105: Fuse the image data of the target tissue corresponding to the different ultrasound beamforming methods to obtain a fused ultrasound image of the target tissue.

In this embodiment, after the image data of the target tissue corresponding to the different ultrasound beamforming methods is obtained, the obtained image data may further be fused. Fusion may be performed directly according to the image data or according to the ultrasound images generated according to the image data. In the fusion process, the advantages of the beamforming methods may be retained according to a preset rule or by means of adaptive calculation, so that the obtained fused ultrasound image can integrate the advantages of the beamforming methods. It may be understood that each pixel in the fused ultrasound image reflects a result of the combined action of the different ultrasound beamforming methods used, and the fused ultrasound image of the target tissue obtained through such fusion will be better than an ultrasound image of the target tissue obtained using a single ultrasound beamforming method.

When the fusion is performed according to the preset rule, a fusing coefficient is usually predetermined. Fusion coefficients corresponding to the beamforming methods may be preset according to clinical experience. For example, three different beamforming methods are used, namely, the DAS beamforming method, the MV beamforming method, and the CF beamforming method. For example, it is preset according to clinical experience that a fusion coefficient corresponding to the DAS beamforming method is $\omega_1$, a fusion coefficient corresponding to the MV beamforming method is $\omega_2$, and a fusion coefficient corresponding to the CF beamforming method is $\omega_3$. Alternatively, the fusion coefficients corresponding to the beamforming methods may be determined by means of machine learning according to the collected image data. For example, three different beamforming methods are still used, namely, the DAS beamforming method, the MV beamforming method, and the CF beamforming method. Specifically, a fusion coefficient model may be constructed, in which the image data obtained using the DAS beamforming method, the image data obtained using the MV beamforming method, and the image data obtained using the CF beamforming method are used as inputs, and a fused ultrasound image is an output. The optimal quality of the fused ultrasound image is used as a training objective to perform iterative training on a training set to continuously adjust the fusion coefficients corresponding to the beamforming methods until convergence, and fusion coefficients at this time are determined as the fusion coefficients corresponding to the beamforming methods.

It may be understood that there may be a difference in the performance of the same ultrasound beamforming method in different application scenarios. For example, in a first application scenario, an ultrasound beamforming method A is better than an ultrasound beamforming method B, while in a second application scenario, the ultrasound beamforming method B is better than the ultrasound beamforming method A. Therefore, the fusion coefficients corresponding to the ultrasound beamforming methods are determined according to an application scenario, which helps further improve the quality of the fused ultrasound image of the target tissue.

In an optional implementation, fusion coefficients corresponding to the different ultrasound beamforming methods may be determined according to an application scenario, where the application scenario may be determined according to one or more of a probe type, a scanning mode, a frequency of probe, and a scanning depth; and then the image data of the target tissue corresponding to the different ultrasound beamforming methods is fused using the fusion coefficients. Specifically, the fusion coefficients corresponding to the beamforming methods in each application scenario may be preset according to clinical experience, or the fusion coefficients corresponding to the beamforming methods in each application scenario may be obtained through training by means of machine learning.

When the fusion is performed by means of adaptive calculation, the fusion coefficients will adaptively change depending on the obtained image data, so as to retain the advantages of the beamforming methods to the greatest extent and obtain a high-quality fused ultrasound image. In an optional implementation, the fusion may be performed according to the ultrasound images generated according to the image data, that is, initial ultrasound images of the target tissue corresponding to the ultrasound beamforming methods are first generated according to the obtained image data. After the initial ultrasound images corresponding to the different ultrasound beamforming methods are obtained, the initial ultrasound images may be fused on a per-pixel basis and according to a pixel value of a pixel, or the initial ultrasound images may be fused on a per-image basis and according to image characteristic. For example, when the fusion is performed on a per-pixel basis and according to a pixel value of a pixel, for a pixel located at the tissue boundary, a weight of the MV beamforming method may be increased, and a weight of the DAS beamforming method may be reduced; and for a pixel located at the background of the image, the weight of the MV beamforming method may be reduced, and the weight of the DAS beamforming method may be increased. When the fusion is performed according to image characteristic, weights of high-frequency information for representing an image detail feature and low-frequency information for representing an overall structural feature of the image may be increased, and a weight for representing noise information of the image may be reduced.

According to the ultrasound beamforming method provided in this embodiment, on the basis of the foregoing embodiment, the image data of the target tissue corresponding to the different ultrasound beamforming methods may be further fused. During the fusion process, the advantages of the beamforming methods are retained to obtain the fused ultrasound image that can integrate the advantages of the beamforming methods, improving the quality of ultrasound imaging.

It should be noted that the embodiments shown in FIG. 7 and FIG. 8 may be combined with each other. In other words, after the image data of the target tissue corresponding to the different ultrasound beamforming methods is obtained, both the initial ultrasound images of the target tissue corresponding to the different ultrasound beamforming methods, and the fused ultrasound image of the target tissue may be generated. Further, the fused ultrasound image of the target tissue and the initial ultrasound images may be displayed in the display interface simultaneously or sequentially, so that the user can selectively view or compare as required.

The ultrasound imaging device can support many ultrasound beamforming methods. If all the ultrasound beamforming methods are used to process the channel data, it will undoubtedly bring huge challenges to the computing power of the ultrasound imaging device. How are the ultrasound beamforming methods for processing the same channel data determined? In an optional implementation, before the channel data is processed using the at least two different ultrasound beamforming methods, a plurality of ultrasound beamforming methods are displayed in the form of text or icons in the display interface for the user to select, and the at least two different ultrasound beamforming methods are determined according to the user's selection operation. Referring to FIG. 9, all the ultrasound beamforming methods supported by the ultrasound imaging device may be displayed for selection by the user. According to this, the user may choose the ultrasound beamforming methods independently according to clinical experience.

Different tissues often have different imaging characteristics. For example, some tissues can form a strongly reflective ultrasound signal, while some tissues can form a weakly reflective ultrasound signal. Also, requirements for the ultrasound examination of different tissues are often different. For example, for some tissues, only an overall structure needs to be viewed, while for some tissues, local details need to be viewed. Combining the imaging characteristics and examination requirements of the tissue to determine the ultrasound beamforming methods to be used will make the ultrasound beamforming methods more in line with the tissue, which helps further improve the quality of ultrasound imaging. For example, the CF beamforming method and the MV beamforming method may be used for a tissue that can form a strongly reflective ultrasound signal and has local details to be viewed.

A mapping relationship between a type of tissue and an ultrasound beamforming method may be pre-established according to imaging characteristics and examination requirements of a tissue, to associate the type of tissue with the ultrasound beamforming methods used. The type of tissue may be represented by an examination site, such as heart, liver, or uterus, or may be represented in other manners, e.g., represented by an ultrasound examination item. Table 1 is an illustration of a mapping relationship. As shown in Table 1, when the type of the target tissue is the heart, three ultrasound beamforming methods A, B, and C are to be used to process the channel data of the target tissue; and when the type of the target tissue is the liver, four ultrasound beamforming methods A, C, D, and F are to be used to process the channel data of the target tissue.

TABLE 1

| Type of tissue | Ultrasound beamforming methods |
| --- | --- |
| Heart | A, B, C |
| Liver | A, C, D, F |
| Uterus | E, F |

In an optional implementation, to improve the quality of ultrasound imaging, before the channel data is processed using the at least two different ultrasound beamforming methods, the type of the target tissue may be obtained, and the at least two different ultrasound beamforming methods may be determined according to the type of the target tissue and a pre-established mapping relationship between a type of tissue and an ultrasound beamforming method. The type of the target tissue may be automatically determined by the ultrasound imaging device according to the echo data, the image obtained or other information, or be determined according to the input of the user. For example, the type of the target tissue may be determined according to the obtained channel data of the target tissue, or may be determined according to the user's input during an ultrasound examination. If the user inputs an instruction to perform breast ultrasound examination, the type of the target tissue is the breast. Optionally, after the at least two different ultrasound beamforming methods are determined according to the mapping relationship, the determined ultrasound beamforming methods may further be displayed in the display interface in the form of text or icons for the user to view.

In another optional implementation, before the channel data is processed using the at least two different ultrasound beamforming methods, the at least two different ultrasound beamforming methods may be first determined according to a type of the target tissue and a pre-established mapping relationship between a type of tissue and an ultrasound beamforming method, and then the determined at least two different ultrasound beamforming methods are displayed in the form of text or icons in the display interface for the user to select, and the final ultrasound beamforming methods for processing the channel data are determined according to the user's selection operation. Taking the mapping relationship shown in Table 1 as an example, when the type of the target tissue is the liver, the four ultrasound beamforming methods A, C, D, and F will be displayed for the user to select. If the user selects A and F, the two ultrasound beamforming methods A and F will be finally used to process the channel data of the target tissue. Taking the mapping relationship shown in Table 1 as an example, when the type of the target tissue is the liver, as shown in FIG. 9, all the ultrasound beamforming methods supported by the ultrasound imaging device may be displayed in the display interface, and the four ultrasound beamforming methods A, C, D, and F are displayed as default options.

On the basis of the embodiment shown in FIG. 8, the following will further elaborate on how to perform fusion according to the initial ultrasound images generated from the image data from two aspects: according to a pixel value of a pixel and according to image characteristic, so as to obtain a high-quality fused ultrasound image.

Referring to FIG. 10, after the initial ultrasound images of the target tissue corresponding to the ultrasound beamforming methods are generated according to the image data, fusing the initial ultrasound images according to a pixel value of a pixel to obtain the fused ultrasound image of the target tissue may specifically include the following steps.

S201: For each pixel in each initial ultrasound image, determine a fusion coefficient of the pixel according to contrast and pixel quality of the pixel, to obtain fusion coefficient maps corresponding to the initial ultrasound images, where the contrast is positively correlated with a pixel value change amount of the pixel relative to a neighboring pixel, the pixel quality is negatively correlated with a difference between a pixel value of the pixel and a pixel median value, and the fusion coefficient is positively correlated with each of the contrast and the pixel quality.

The "fusion coefficient map" mentioned here refers to the collection of the fusion coefficients corresponding to the pixels in the initial ultrasound images. However, it does not mean that the fusion coefficient map is necessarily an "image" formed by the fusion coefficients.

When N ($N \geq 2$) different ultrasound beamforming methods are used to process the same channel data obtained from the target tissue, N initial ultrasound images of a same size will be obtained. The initial ultrasound image may be a grayscale image or a color image; or may be a two-dimensional image or a three-dimensional image.

In this embodiment, on a per-pixel basis, for each pixel in each initial ultrasound image, a fusion coefficient of the pixel is determined according to contrast and pixel quality of the pixel. The contrast may be determined according to a pixel value change amount between the pixel and a neighboring pixel. For example, in a two-dimensional image, the contrast may be determined according to pixel differences between the pixel and four neighboring pixels at the top, bottom, left, and right of the pixel; and in a three-dimensional image, the contrast may be determined according to pixel differences between the pixel and six neighboring pixels at the top, bottom, left, right, front, and back of the pixel. The neighboring pixel may also be another pixel in a 9-square grid centered at the pixel. A quantity of neighboring pixels used in determining the contrast may be selected as required, which is not limited herein. The contrast is positively correlated with the pixel value change amount, that is, the larger the pixel difference between the pixel and the neighboring pixel, the higher the contrast. The fusion coefficient is positively correlated with the contrast, that is, the higher the contrast, the larger the fusion coefficient. Taking the DAS beamforming method and the MV beamforming method as an example, for a pixel at the tissue boundary, contrast in an initial ultrasound image obtained using the MV beamforming method will be greater than that in an initial ultrasound image obtained using the DAS beamforming method. Therefore, setting a fusion coefficient positively correlated with the contrast allows the detail information of the target tissue to be better displayed.

Taking a grayscale image as an example, the human eye is most comfortable with the middle gray value, and the image being too bright or too dark will affect the human eye's recognition of a tissue. The closer a pixel is to the middle gray value, the higher the pixel quality; and the further a pixel is away from the middle gray value, the lower the pixel quality. In other words, the pixel quality is negatively correlated with the difference between the pixel value of the pixel and the pixel median value. The pixel median value may be preset. For example, for a grayscale image, the pixel median value may be set to the middle gray value of 128; and for a normalized grayscale image, the pixel median value may be set to 0.5. Alternatively, the pixel median value may be calculated according to the initial ultrasound image, and a median value of all pixel values in the initial ultrasound image may be determined as the pixel median value. Still taking the DAS beamforming method and the MV beamforming method as an example, for a pixel at the image background, the pixel quality in the initial ultrasound image obtained using the DAS beamforming method will be higher than that in the initial ultrasound image obtained using the MV beamforming method. Therefore, setting a fusion coefficient positively correlated with the pixel quality allows the overall structural information of the target tissue to be better displayed.

The fusion coefficients are in a one-to-one correspondence with the pixels. After the fusion coefficient of each pixel is determined, the fusion coefficients are arranged according to a position relationship of the pixels, and N fusion coefficient maps having the same size as and in a one-to-one correspondence with the N initial ultrasound images will be obtained. If the initial ultrasound image is a three-dimensional image, the resulting fusion coefficient map is also a three-dimensional image.

S202: Fuse all the obtained initial ultrasound images of the target tissue according to the obtained fusion coefficient maps corresponding to the initial ultrasound images to obtain the fused ultrasound image of the target tissue.

In an optional implementation, the fusion coefficients in the fusion coefficient map may be used as weights to perform weighted fusion on the initial ultrasound images. Pixel values at a same position in the N initial ultrasound images may be weighted summed according to the corresponding fusion coefficients, that is, a pixel value of each pixel in the fused ultrasound image is a sum of products of pixel values at a position of the pixel in all the initial ultrasound images and corresponding fusion coefficients.

According to the ultrasound beamforming method provided in this embodiment, after the initial ultrasound images are obtained, the contrast and pixel quality of each pixel are further determined on a per-pixel basis, and the initial ultrasound images are fused by using the fusion coefficients positively correlated with the contrast and pixel quality, so that the fused ultrasound image can better display the overall structural information and detail information of the target tissue.

For example, the initial ultrasound images generated are N ($N \geq 2$) two-dimensional grayscale images in the following specific description of how to fuse the initial ultrasound images according to a pixel value of a pixel to obtain the fused ultrasound image of the target tissue.

Assuming that a normalized grayscale value of a pixel (x, y) in an $i^{th}$ initial ultrasound image is $g_i(x, y)$, contrast $c_i(x, y)$ of the pixel (x, y) may be determined according to the following formula:

$$c_i(x, y) = \qquad\qquad\qquad\qquad\qquad\qquad (1)$$
$$|g_i(x, y-1) + g_i(x-1, y) + g_i(x+1, y) + g_i(x, y+1) - 4g_i(x, y)|/4$$

In other words, the contrast $c_i(x, y)$ of the pixel (x, y) is differences between normalized gray values of the pixel and the four neighboring pixels at the top, bottom, left, and right of the pixel. When the normalized gray value of the pixel changes greatly, for example, when the pixel is located at the boundary of the target tissue, $c_i(x, y)$ has a relatively large value.

Pixel quality $q_i(x, y)$ of the pixel (x, y) may be determined according to the following formula:

$$q_i(x, y) = e^{\frac{-(g_i(x,y)-\mu)^2}{2\sigma^2}} \qquad\qquad\qquad (2)$$

where $\mu$ represents the pixel median value ranging from 0 to 1. When the normalized gray value of the pixel is closer to $\mu$, the pixel quality $q_i(x, y)$ is higher and closer to 1; and when the normalized gray value of the pixel is further away from $\mu$, the pixel quality $q_i(x, y)$ is lower and closer to 0. The human eye is most comfortable with a pixel having the middle gray value, and the pixel being too bright or too dark will affect the human eye's recognition of a tissue. Therefore, for the normalized gray value, $\mu$ may be set to 0.5. $\sigma$ represents a variance ranging from 0 to 1. The smaller $\sigma$, the faster the pixel quality $q_i(x, y)$ falls as the normalized gray value $g_i(x, y)$ of the pixel is further away from $\mu$. The larger $\sigma$, the slower the pixel quality $q_i(x, y)$ falls as the normalized gray value $g_i(x, y)$ of the pixel is further away from $\mu$. Preferably, the value of $\sigma$ may be between 0.1 and 0.2.

After the contrast $c_i(x, y)$ and the pixel quality $q_i(x, y)$ of the pixel $(x, y)$ are determined, a quality coefficient $cq_i(x, y)$ of the pixel $(x, y)$ may be determined according to the following formula, and the quality coefficient $cq_i(x, y)$ is used to reflect the quality of the pixel $(x, y)$.

$$cq_i(x, y) = c_i(x, y)^{w_c} * q_i(x, y)^{w_q} \qquad (3)$$

where $w_c$ represents a weight of the contrast ranging from 0 to 1; and $w_q$ represents a weight of the pixel quality ranging from 0 to 1. The values of $w_c$ and $w_q$ may be determined according to fusion requirements. For example, when more attention is needed to the detail information of the target tissue, $w_c$ may be reduced, and $w_q$ may be increased; and when more attention is needed to the overall structural information of the target tissue, $w_c$ may be increased, and $w_q$ may be reduced.

Then, a fusion coefficient $w_i(x, y)$ is calculated according to the quality coefficient of each initial ultrasound image according to the following expression:

$$w_i(x, y) = \frac{cq_i(x, y)}{\sum_{i=1}^{N} cq_i(x, y)} \qquad (4)$$

When quality coefficients $w_i(x, y)$ $(i=1, 2, \ldots, N)$ of the pixel $(x, y)$ are all very poor, e.g., are all less than a threshold $\varepsilon$, fusion coefficients calculated according to the formula (4) will make no sense. In this case, average fusion may be performed, that is, $$w_i(x, y) = \frac{1}{N}.$$

This can not only reduce a calculation amount of calculating the fusion coefficients, but also help improve the fusion quality.

Finally, according to the following expression, all pixels in the N initial ultrasound images may be fused according to the fusion coefficients to obtain a normalized gray value $g(x, y)$ of the pixel $(x, y)$ in the fused ultrasound image of the target tissue:

$$g(x, y) = \sum_{i=1}^{N} w_i(x, y) * g_i(x, y) \qquad (5)$$

Figure 11:
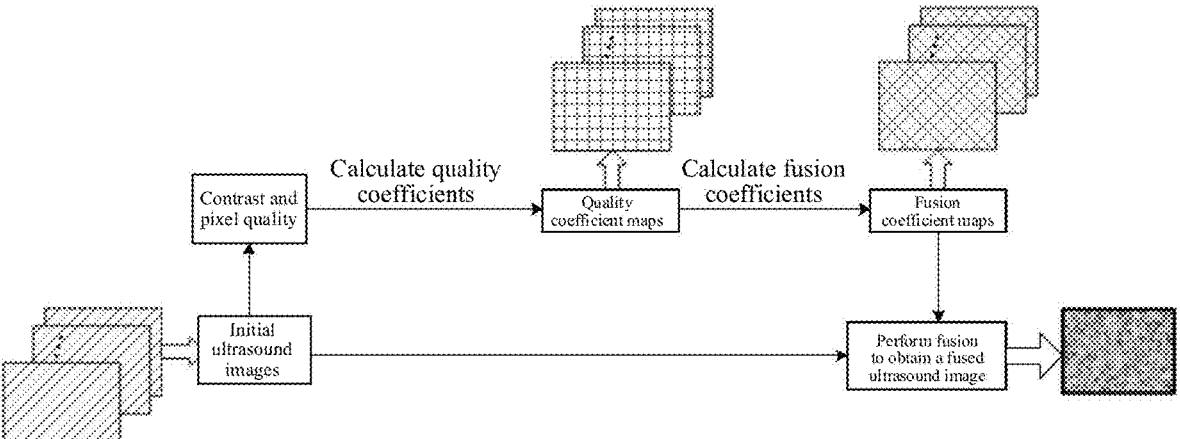
FIG. 11 is a schematic diagram of a process of fusing initial ultrasound images according to a pixel value of a pixel according to an embodiment of the disclosure.

For the above-mentioned process of fusing the initial ultrasound images according to the pixel value of the pixel, reference may be made to FIG. 11. For each pixel in the initial ultrasound images, contrast and pixel quality are first calculated, then a quality coefficient is calculated according to the contrast and pixel quality to obtain a quality coefficient map, then a fusion coefficient is calculated according to the quality coefficient map to obtain a fusion coefficient map, and finally the initial ultrasound images are fused according to the fusion coefficient map to obtain a fused ultrasound image of the target tissue.

Figure 12:
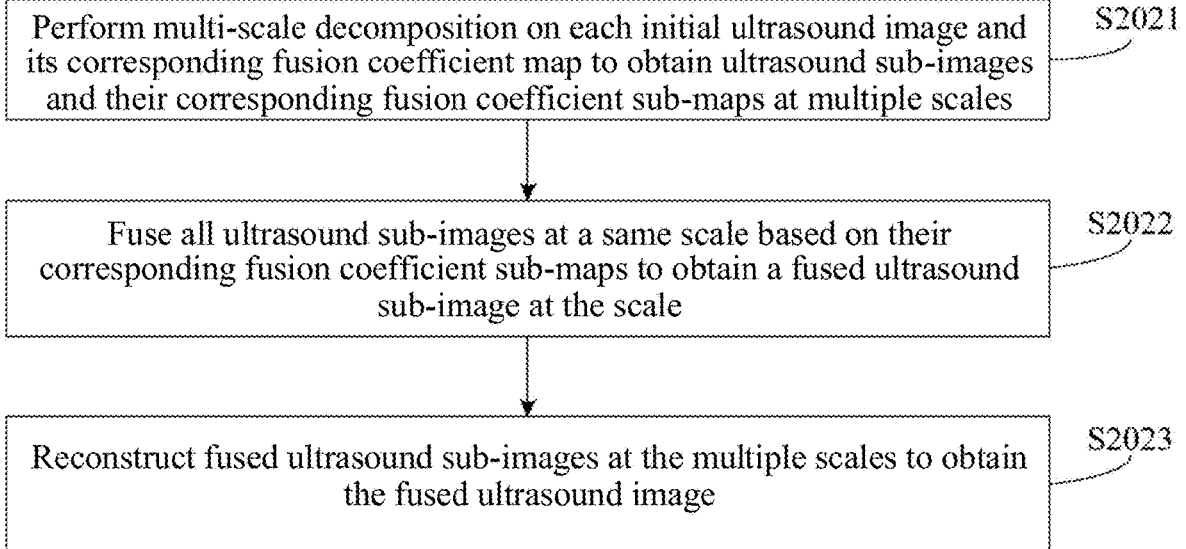
FIG. 12 is a flowchart of multi-scale fusion according to an embodiment of the disclosure.

To eliminate seams that may be generated in the process of fusing the initial ultrasound images according to the pixel value of the pixel, a multi-scale fusion method may be used for fusion. Referring to FIG. 12, on the basis of the embodiment shown in FIG. 10, in the ultrasound beamforming method provided in this embodiment, fusing all the obtained initial ultrasound images of the target tissue according to the obtained fusion coefficient maps corresponding to the initial ultrasound images may specifically include the following steps.

S2021: Perform multi-scale decomposition on each initial ultrasound image and its corresponding fusion coefficient map to obtain ultrasound sub-images and their corresponding fusion coefficient sub-maps at multiple scales.

In this embodiment, the initial ultrasound image and its corresponding fusion coefficient map are decomposed at a same scale, that is, the ultrasound sub-images and the fusion coefficient sub-maps have the same quantity and the same size and are in a one-to-one correspondence. For example, the $i^{th}$ $(i=1, 2, \ldots, N)$ initial ultrasound image $g_i$ may be decomposed into L scales, and an ultrasound sub-image at a $l^{th}$ scale is $$g_i^l.$$

In this case, a fusion coefficient map $w_i$ corresponding to the $i^{th}$ initial ultrasound image $g_i$ is also decomposed into L scales, and a fusion coefficient sub-map at a $l^{th}$ scale is $$w_i^l.$$

Then there are N ultrasound sub-images and corresponding N fusion coefficient sub-maps at each scale. In this embodiment, a specific method for performing multi-scale decomposition is not limited, for example, may be Laplacian pyramid decomposition, Gaussian pyramid decomposition, wavelet transform decomposition, empirical mode decomposition, etc.

S2022: Fuse all ultrasound sub-images at a same scale according to their corresponding fusion coefficient sub-maps to obtain a fused ultrasound sub-image at the scale.

In this embodiment, the N ultrasound sub-images at the $l^{th}$ scale may be fused according to their corresponding N fusion coefficient sub-maps according to the following formula, to obtain a fused ultrasound sub-image $g^l$ at the $l^{th}$ scale:

$$g^l = \sum_{i=1}^{N} g_i^l * w_i^l \qquad (6)$$

Finally, L fused ultrasound sub-images $g^l$ $(l=1, 2, \ldots, L)$ are obtained.

S2023: Reconstruct fused ultrasound sub-images at the multiple scales to obtain the fused ultrasound image.

After the fused ultrasound sub-images $g^l$ at the L scales are obtained, reconstruction may be performed by stage-wise upsampling from a low-scale image pyramid and summation with a high-scale image pyramid, to finally obtain the fused ultrasound image of the target tissue.

According to the ultrasound beamforming method provided in this embodiment, multi-scale decomposition is further performed on the initial ultrasound images and their corresponding fusion coefficient maps, and the ultrasound sub-images and their corresponding fusion coefficient sub-maps are fused at the same scale, and finally reconstruction is performed according to the fused ultrasound sub-images at the scales to finally determine the fused ultrasound image of the target tissue, so that the seams that may be generated in the process of determining the fusion coefficient on a per-pixel basis and according to the pixel value of the pixel for fusion can be eliminated.

Figure 13:
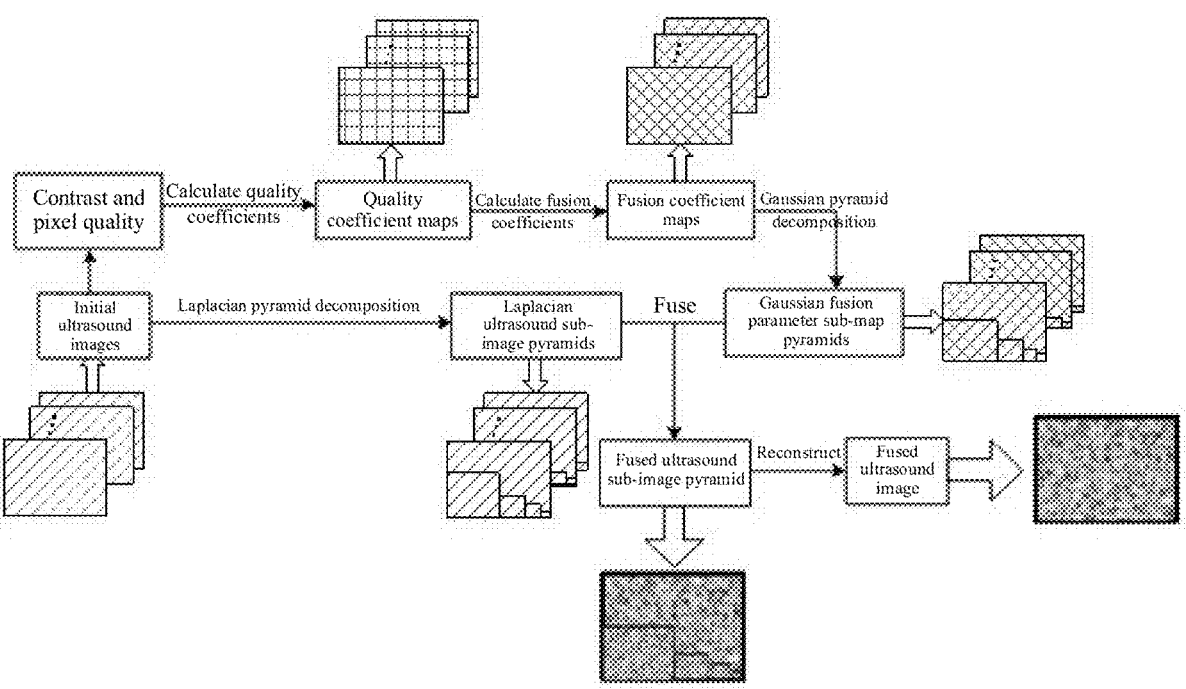
FIG. 13 is a schematic diagram of a process of multi-scale fusion according to an embodiment of the disclosure.

To retain the detail information of the image as much as possible in the process of eliminating the seams, in an optional implementation, Laplacian pyramid decomposition is performed on each initial ultrasound image, and ultrasound sub-images at different scales are used to represent image details at the different scales to retain the detail information of the image as much as possible; and Gaussian pyramid decomposition is performed on the fusion coefficient map corresponding to each initial ultrasound image, and the fusion coefficient sub-maps at the different scales are used to represent low-pass images at the different scales, so as to smoothen the image and eliminate the seams. A specific implementation process is shown in FIG. 13, Laplacian pyramid decomposition is performed on the initial ultrasound images to obtain Laplacian ultrasound sub-image pyramids; fusion coefficient maps are obtained according to the initial ultrasound images, and Gaussian pyramid decomposition is performed on the fusion coefficient maps to obtain Gaussian fusion coefficient sub-map pyramids; the Laplacian ultrasound sub-image pyramids and the Gaussian fusion coefficient sub-map pyramids are fused to obtain a fused ultrasound sub-image pyramid; and reconstruction is performed according to the fused ultrasound sub-image pyramid to obtain a fused ultrasound image.

Figure 14:
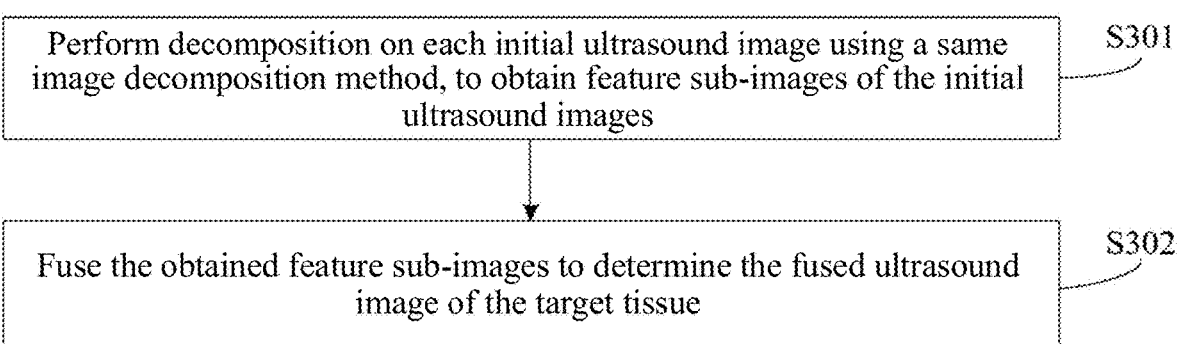
FIG. 14 is a flowchart of fusing initial ultrasound images according to image characteristic according to an embodiment of the disclosure.

Referring to FIG. 14, after the initial ultrasound images of the target tissue corresponding to the ultrasound beamforming methods are generated according to the image data, fusing the initial ultrasound images according to image characteristic to obtain the fused ultrasound image of the target tissue may specifically include the following steps.

S301: Perform decomposition on each initial ultrasound image using a same image decomposition method, to obtain characteristic sub-images of the initial ultrasound images.

Image decomposition methods for decomposing the initial ultrasound images in this embodiment include, but are not limited to, singular value decomposition, wavelet transform decomposition, pyramid decomposition, empirical mode decomposition, and the like. Each characteristic sub-image includes feature information of the initial ultrasound image, such as high-frequency information, low-frequency information, and noise information. All characteristic sub-images of the initial ultrasound image include all feature information of the initial ultrasound image, and the initial ultrasound image can be reconstructed according to all the characteristic sub-images of the initial ultrasound image.

S302: Fuse the obtained characteristic sub-images to determine the fused ultrasound image of the target tissue.

After the characteristic sub-images of the initial ultrasound images are obtained, fusion coefficients may be determined according to the size or importance of the feature information contained in the characteristic sub-images, and then the characteristic sub-images are fused according to the fusion coefficients to finally determine the fused ultrasound image of the target tissue.

Figure 15:
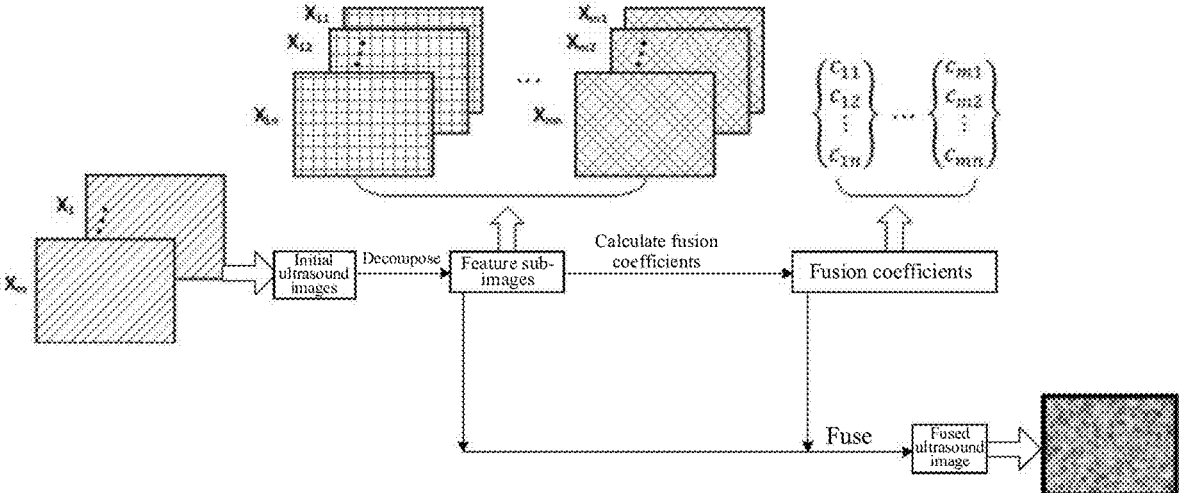
FIG. 15 is a schematic diagram of a process of fusing initial ultrasound images according to image characteristic according to an embodiment of the disclosure.

For a specific implementation process, reference may be made to FIG. 15. m initial ultrasound images are decomposed using a same image decomposition method, and each initial ultrasound image is decomposed into n characteristic sub-images, to obtain m*n characteristic sub-images. Depending on an amount of useful feature information (such as high-frequency information and low-frequency information) contained in the characteristic sub-images, the fusion coefficients of the characteristic sub-images are determined, to obtain m*n fusion coefficients. Weighted fusion of the m*n characteristic sub-images is performed according to the m*n fusion coefficients to obtain the fused ultrasound image of the target tissue.

According to the ultrasound beamforming method provided in this embodiment, after the initial ultrasound images are obtained, the initial ultrasound images are further decomposed into characteristic sub-images containing feature information, and fusion is performed depending on the amount of useful feature information contained in the characteristic sub-images, so that the fused ultrasound image can better display the useful feature information in the target tissue.

In an optional implementation, performing decomposition on each initial ultrasound image using a same image decomposition method, to obtain characteristic sub-images of the initial ultrasound images may specifically include: performing singular value decomposition on each initial ultrasound image to obtain a left singular matrix, a singular value matrix, and a right singular matrix of each of the initial ultrasound images, where the singular value matrix includes a singular value of the initial ultrasound image, the left singular matrix includes a left singular vector corresponding to the singular value in the singular value matrix, and the right singular matrix includes a right singular vector corresponding to the singular value in the singular value matrix; and determining a characteristic sub-image corresponding to the singular value according to the singular value and its corresponding left singular vector and right singular vector to obtain the characteristic sub-images of the initial ultrasound images, where amplitude or energy of the singular value is greater than a preset threshold.

It is assumed that m initial ultrasound images $\{X_1, X_2, \ldots, X_i, \ldots, X_m\}$ are obtained using m ultrasound beamforming methods, and all the initial ultrasound images have the same dimensions, that is, M*N. Singular value decomposition is performed on each of the m initial ultrasound images as follows:

$$X_i = U_i S_i V_i'$$ (7)

where $U_i$ represents a left singular matrix of $X_i$ and is an orthogonal matrix having dimensions of M*M; $V_i$ represents a right singular matrix of $X_i$ and is an orthogonal matrix having dimensions of N*N; and $S_i$ represents a singular value matrix of $X_i$ and is a matrix having dimensions of M*N. Values on the diagonal of the singular value matrix $S_i$ are singular values of the initial ultrasound images $X_i$, and values on the other positions are 0. It is assumed that the singular value matrix $S_i$ includes k singular values $\{s_{i1}, s_{i2}, \ldots, s_{ij}, \ldots, s_{ik}\}$, where k=min{M, N}. According to each singular value and its corresponding left singular vector and right singular vector, a characteristic sub-image corresponding to the singular value may be reconstructed. Taking a singular value $s_{ij}$ as an example, a characteristic sub-image $X_{ij}$ corresponding to the singular value is:

$$X_{ij} = s_{ij} u_{ij} v_{ij}'$$ (8)

where $u_{ij}$ is a vector of a $j^{th}$ column of the left singular matrix $U_i$, and $v_{ij}$ is a vector of a $j^{th}$ column of the right singular matrix $V_i$.

It may be understood that the larger the singular value, the more useful feature information the corresponding characteristic sub-image contains; and the smaller the singular value, the more noise information the corresponding characteristic sub-image contains.

Therefore, to reduce the calculation amount and to avoid introducing too much noise information, reconstruction may be performed only on singular values whose amplitude or energy is greater than a preset threshold. The energy of the singular value may be determined according to the square of the amplitude of the singular value. Singular value decomposition is performed on the m initial ultrasound images to obtain m*n characteristic sub-images, where n≤k.

After the singular value is reconstructed to obtain the characteristic sub-images of the initial ultrasound images, a fusion coefficient of the characteristic sub-image corresponding to the singular value may be determined according to the amplitude or energy of the singular value; and weighted fusion is performed on the obtained characteristic sub-images according to the fusion coefficient to determine the fused ultrasound image of the target tissue.

It may be understood that a larger fusion coefficient should be assigned to a characteristic sub-image containing more useful feature information to enhance the useful feature; and a smaller fusion coefficient should be assigned to a characteristic sub-image containing more noise information to reduce noise interference. Therefore, the fusion coefficient of the characteristic sub-image may be positively correlated with the amplitude or energy of the singular value.

In an optional implementation, a fusion coefficient $c_{ij}$ of a characteristic sub-image $X_{ij}$ corresponding to the singular value $s_{ij}$ may be determined according to the following formula:

$$c_{ij} = \frac{s_{ij}}{\sum_{i=1}^{m} \sum_{j=1}^{n} s_{ij}} \quad (9)$$

The formula (9) determines the fusion coefficient according to the amplitude of the singular value. Alternatively, the fusion coefficient may be determined according to the energy of the singular value.

After the characteristic sub-images and their corresponding fusion coefficients are obtained, image fusion may be performed according to the following formula to determine the fused ultrasound image X of the target tissue:

$$X = \sum_{i=1,j=1}^{i=m,j=n} c_{ij}X_{ij} \quad (10)$$

In another optional implementation, performing decomposition on each initial ultrasound image using a same image decomposition method, to obtain characteristic sub-images of the initial ultrasound images may specifically include: performing wavelet decomposition on each initial ultrasound image using a same wavelet base and decomposition level, and determining a characteristic sub-image for representing an overall structural feature, a characteristic sub-image for representing a local detail feature in a horizontal direction, a characteristic sub-image for representing a local detail feature in a vertical direction, and a characteristic sub-image for representing a local detail feature in a diagonal direction at each decomposition level, to obtain the characteristic sub-images of the initial ultrasound images.

Figure 16:
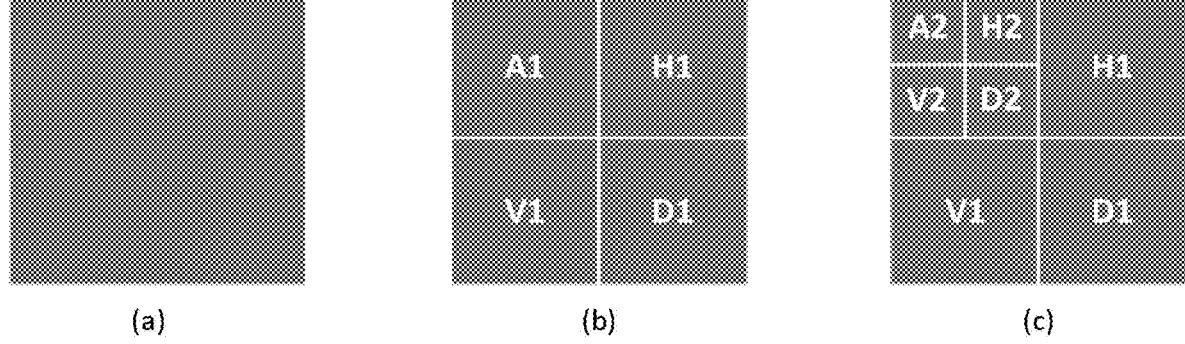
FIG. 16 is a schematic diagram of wavelet decomposition according to an embodiment of the disclosure.

The wavelet decomposition of the initial ultrasound image can extract the useful feature information contained in the initial ultrasound image, such as the overall structural feature (low-frequency information) and the local detail feature (high-frequency information) of the initial ultrasound image. Referring to FIG. 16, (a) in FIG. 16 represents an initial ultrasound image, and when a first layer of wavelet transform decomposition of (a) is implemented, four characteristic sub-images as shown in (b) can be obtained: A1 is a characteristic sub-image for representing an overall structural feature of (a), H1 is a characteristic sub-image for representing a local detail feature in a horizontal direction of (a), V1 is a characteristic sub-image for representing a local detail feature in a vertical direction of (a), and D1 is a characteristic sub-image for representing a local detail feature in a diagonal direction of (a). If a second layer of wavelet transform decomposition continues to be implemented, that is, wavelet transform decomposition continues to be implemented on A1, four characteristic sub-images as shown in (c) may be further obtained: A2 is a characteristic sub-image for representing an overall structural feature of A1, H2 is a characteristic sub-image for representing a local detail feature in a horizontal direction of A1, V2 is a characteristic sub-image for representing a local detail feature in a vertical direction of A1, and D2 is a characteristic sub-image for representing a local detail feature in a diagonal direction of A1. If a third layer of wavelet transform decomposition continues to be implemented, that is, wavelet transform decomposition continues to be implemented on A2, the result may be inferred by analogy, and details are not described herein. For example, if the two layers of wavelet transform decomposition are performed on (a), characteristic sub-images of (a) will include: A2, H2, H1, V2, V1, D2, and D1.

It should be noted that this embodiment does not limit the type of a wavelet base and a quantity of decomposition levels used for wavelet decomposition, but the wavelet base and decomposition level used for wavelet decomposition of each initial ultrasound image must be the same. Each time wavelet transform decomposition is performed on the image, the dimensions of the image will be halved. Starting from the second layer of wavelet transform decomposition, the implementation of wavelet transform decomposition is to perform wavelet transform decomposition on a characteristic sub-image obtained in the previous layer and used for representing the overall structural feature. Therefore, when the decomposition level is greater than 1, the dimensions of the characteristic sub-images of the initial ultrasound image will not be exactly the same.

n-level wavelet decomposition is performed on each of the m initial ultrasound images $\{X_1, X_2, \ldots, X_i, \ldots, X_m\}$ to obtain different characteristic sub-images of each initial ultrasound image, where n is a quantity of decomposition levels. All characteristic sub-images of the $i^{th}$ initial ultrasound image are defined by $\{An_i, H1_i, \ldots, Hn_i, V1_i, \ldots, Vn_i, D1_i, \ldots, Dn_i\}$.

After wavelet decomposition is performed on the initial ultrasound images to obtain the characteristic sub-images of the initial ultrasound images, characteristic sub-images located at a same decomposition level and used for representing a same type of feature may be fused according to fusion coefficients, to obtain a fused characteristic sub-image at each decomposition level, where the fusion coefficient is a preset fusion coefficient or is determined according to amplitude of the characteristic sub-image; and inverse wavelet transform is performed on fused characteristic sub-images at all decomposition levels to determine the fused ultrasound image of the target tissue.

The fusion coefficient may be preset according to experience, or the fusion coefficient may be calculated according to the amplitude of the characteristic sub-image. The larger the amplitude of the characteristic sub-image, the larger the corresponding fusion coefficient. It should be noted that only the characteristic sub-images located in the same decomposition level and used for representing the same type of features can be fused. For example, m characteristic sub-images $An_i$ (i=1 to m) located in an $n^{th}$ decomposition level and used for representing the overall structural feature are fused, m characteristic sub-images $H1_i$ (i=1 to m) located in a first decomposition level and used for representing the local detail feature in the horizontal direction are fused, and m characteristic sub-images $V2_i$ (i=1 to m) located in a second decomposition level and used for representing the local detail feature in the vertical direction are fused, . . . , and so on, and details are not described herein.

For example, when the m characteristic sub-images $An_i$ (i=1 to m) located in the $n^{th}$ decomposition level and used for representing the overall structural feature are fused, a fusion coefficient cni corresponding to the characteristic sub-image $An_i$ may be calculated according to the following formula:

$$cn_i = \frac{\text{sum}(An_i)}{\sum_{i=1}^{m}\text{sum}(An_i)} \qquad (11)$$

where $\text{sum}(An_i)$ represents a sum of all pixels in the characteristic sub-image $An_i$. The fusion coefficient corresponding to each characteristic sub-image may be calculated according to the formula (11), and then the characteristic sub-images located in the same decomposition level and used for representing the same type of feature may be fused, so that the fused characteristic sub-images at the decomposition levels can be obtained. The fused characteristic sub-image {An, H1, . . . , Hn, V1, . . . , Vn, D1, . . . , Dn} will be obtained by fusing the characteristic sub-images of the m initial ultrasound images. Taking An as an example, the fusion process is as follows:

$$An = \sum_{i=1}^{m} cn_i An_i \qquad (12)$$

For the fusion process of other fused characteristic sub-images, reference may be made to the formula (12), and details are not described herein.

Finally, the inverse wavelet transform is performed on the obtained fused characteristic sub-image {An, H1, . . . , Hn, V1, . . . , Vn, D1, . . . , Dn}, and the fused ultrasound image of the target tissue may be obtained.

In still another optional implementation, performing decomposition on each initial ultrasound image using a same image decomposition method, to obtain characteristic sub-images of the initial ultrasound images may specifically include: decomposing each initial ultrasound image using a same empirical mode decomposition method, and determining a preset quantity of detail characteristic sub-images for representing image detail information at different scales and one structural characteristic sub-image containing image brightness information, to obtain the characteristic sub-images of the initial ultrasound images, where the detail characteristic sub-image is determined according to an intrinsic mode function component, and the structural characteristic sub-image is determined according to a decomposition residual.

The same empirical mode decomposition is performed on each of the m initial ultrasound images {$X_1$, $X_2$, . . . , $X_i$, . . . , $X_m$}, so that a series of characteristic sub-images can be obtained. For example, if the quantity of decomposition layers is n, n detail characteristic sub-images for representing image detail information at different scales and one structural characteristic sub-image containing image brightness information will be obtained, where the detail characteristic sub-image is determined according to an intrinsic mode function component, and the structural characteristic sub-image is determined according to a decomposition residual. All characteristic sub-images of the $i^{th}$ initial ultrasound image $X_i$ are defined by {$IMF_{i1}$, $IMF_{i2}$, . . . , $IMF_{in}$, $Res_i$}, where IMF is referred to as an intrinsic mode function in the field of empirical mode decomposition, and Res is a decomposition residual. For the convenience of mathematical notation, $Res_i$ may be written as $IMF_{i(n+1)}$, and then:

$$X_i = \sum_{j=1}^{n+1} IMF_{ij} \qquad (13)$$

$IMF_{ij}$ (1≤j≤n) is a detail characteristic sub-image determined according to the intrinsic mode function component and containing the detail information of the image at the different scales, $IMF_{ij}$ (j=n+1) is a structural characteristic sub-image determined according to the decomposition residual and containing the structural information of the image, and $IMF_{ij}$ has the same dimensions as the initial ultrasound image.

After empirical mode decomposition is performed on the initial ultrasound images to obtain the characteristic sub-images of the initial ultrasound images, detail characteristic sub-images may be fused at a same scale, and a fused detail characteristic sub-image at each scale may be determined, to obtain a preset quantity of fused detail characteristic sub-images; the obtained structural characteristic sub-images are fused to obtain one fused structural characteristic sub-image; and reconstruction is performed according to the preset quantity of fused detail characteristic sub-images and the one fused structural characteristic sub-image, to determine the fused ultrasound image of the target tissue.

The fusion coefficient may be preset according to experience, or the fusion coefficient may be calculated according to the amplitude of the characteristic sub-image. The larger the amplitude of the characteristic sub-image, the larger the corresponding fusion coefficient. A fusion coefficient $c_{ij}$ corresponding to the characteristic sub-image $IMF_{ij}$ may be calculated according to the following formula:

$$c_{ij} = \frac{\text{sum}(IMF_{ij})}{\sum_{i=1}^{m}\text{sum}(IMF_{ij})} \qquad (14)$$

where $\text{sum}(IMF_{ij})$ represents a sum of all pixels in the characteristic sub-image $IMF_{ij}$. The fusion coefficients corresponding to each detail characteristic sub-image and structural characteristic sub-image may be calculated according to the formula (14). Then fusion is performed according to the fusion coefficients to determine the fused ultrasound image X of the target tissue, and the fusion process is as follows:

$$X = \sum_{j=1}^{n+1} \sum_{i=1}^{m} c_{ij} IMF_{ij} \qquad (15)$$

In an embodiment, alternatively, before the image data is obtained, the beamformed data obtained using the different beamforming methods may be directly fused, that is, after the channel data of the target tissue is obtained, the at least two different ultrasound beamforming methods may be used to perform at least two beamforming processes on the same channel data to obtain at least two groups of beamformed data of the target tissue corresponding to the at least two different ultrasound beamforming methods. The at least two beamforming processes are performed on the same channel data, and each ultrasound beamforming method can correspondingly obtain one group of beamformed data. Here, the at least two different ultrasound beamforming methods are different in at least one of principle, step, and parameter.

The at least two groups of beamformed data of the target tissue corresponding to the at least two different ultrasound beamforming methods are fused to obtain the fused beamformed data of the target tissue, and the ultrasound image of target tissue is generated according to the fused beamformed data. Here, the beamformed data may be data in any step after beamforming and before forming ultrasound image data.

In this embodiment, for the obtaining of the channel data, the specific beamforming method, the determination of the beamforming methods, the determination of the fusion coefficients, and the specific method for fusion, reference may be made to the applicable method described above, and details are not detailed herein again.

The description has been made with reference to various example embodiments herein. However, persons skilled in the art should appreciate that changes and modifications may be made to the example embodiments without departing from the scope herein. For example, various operation steps and assemblies for executing operation steps may be implemented in different ways according to a specific application or considering any number of cost functions associated with the operation of the system (for example, one or more steps may be deleted, modified, or incorporated into other steps).

In addition, as understood by persons skilled in the art, the principles herein may be reflected in a computer program product on a computer-readable storage medium that is pre-loaded with computer-readable program codes. Any tangible, non-transitory computer-readable storage medium may be used, including magnetic storage devices (hard disks, floppy disks, and the like), optical storage devices (CD-ROM, DVD, Blu-ray disks, and the like), flash memories, and/or the like. These computer program instructions can be loaded onto a general-purpose computer, a dedicated computer, or other programmable data processing apparatus to form a machine, such that these instructions executed on a computer or other programmable data processing apparatus can generate an apparatus that implements a specified function. These computer program instructions may also be stored in a computer-readable memory that may instruct a computer or other programmable data processing apparatus to operate in a specific manner, such that the instructions stored in the computer-readable memory may form a manufactured product, including an implementation apparatus that implements a specified function. The computer program instructions may also be loaded onto a computer or other programmable data processing apparatus, such that a series of operating steps are executed on the computer or other programmable device to produce a computer-implemented process, such that the instructions executed on the computer or other programmable device can provide steps for implementing a specified function.

Although the principles herein have been shown in various embodiments, many modifications of structures, arrangements, ratios, elements, materials, and components that are particularly suitable for specific environments and operating requirements can be made without departing from the principles and scope of the disclosure. The above modifications and other changes or amendments will be included within the scope herein.

The above specific description has been described with reference to various embodiments. However, persons skilled in the art would have appreciated that various modifications and changes could have been made without departing from the scope of the disclosure. Therefore, consideration of the disclosure will be in an illustrative rather than a restrictive sense, and all such modifications will be included within the scope thereof. Likewise, the advantages of various embodiments, other advantages, and the solutions to problems have been described above. However, the benefits, advantages, solutions to problems, and any elements that can produce these, or solutions that make them more explicit, should not be interpreted as critical, necessary, or essential. The term "comprise", "include", and any other variants thereof used herein are non-exclusive, so that the process, method, document, or device that includes a list of elements includes not only these elements, but also other elements that are not explicitly listed or do not belong to the process, method, system, document, or device. Furthermore, the term "coupling" and any other variations thereof used herein refer to physical connection, electrical connection, magnetic connection, optical connection, communication connection, functional connection, and/or any other connection.

The disclosure has been described by using specific examples above, which are merely for the purpose of facilitating understanding of the disclosure and are not intended to limit the disclosure. For a person skilled in the technical field to which the disclosure belongs, several simple deductions, variations, or replacements may also be made according to the idea of the disclosure.

What is claimed is:

1. An ultrasound beamforming method, comprising:
obtaining channel data from echoes returned from a target tissue;
obtaining a type of the target tissue and determining at least two different ultrasound beamforming methods according to the type of the target tissue and a pre-established mapping relationship between a type of tissue and an ultrasound beamforming method; and
performing at least two beamforming processes on the channel data using the at least two different ultrasound beamforming methods to obtain at least two image data frames of the target tissue corresponding to the at least two different ultrasound beamforming methods, wherein the at least two beamforming processes are performed on same channel data, and each of the at least two different ultrasound beamforming methods correspondingly obtains one image data frame, and the at least two different ultrasound beamforming methods are different in at least one of a principle, a step, and a parameter.

2. The method of claim 1, further comprising:

fusing the at least two image data frames to obtain a fused ultrasound image of the target tissue.

3. The method of claim 2, wherein fusing the at least two image data frames comprises:

determining fusion coefficients corresponding to the at least two different ultrasound beamforming methods according to an application scenario, wherein the application scenario is determined according to one or more of a probe type, a scanning mode, a frequency of probe, and a scanning depth; and fusing the at least two image data frames of the target tissue using the fusion coefficients.

4. The method of claim 2, wherein fusing the at least two image data frames of the target tissue to obtain the fused ultrasound image of the target tissue comprises:

respectively generating, according to the at least two image data frames, at least two initial ultrasound images of the target tissue corresponding to the at least two ultrasound beamforming methods; and fusing the at least two initial ultrasound images according to pixel values or according to an image characteristic to obtain the fused ultrasound image of the target tissue.

5. The method of claim 4, wherein fusing the at least two initial ultrasound images according to pixel values to obtain the fused ultrasound image of the target tissue comprises:

for each pixel in each initial ultrasound image, determining a fusion coefficient of the pixel according to a contrast and a pixel quality of the pixel, to obtain fusion coefficient maps corresponding to the at least two initial ultrasound images, wherein the contrast is positively correlated with a pixel value change amount of the pixel relative to a neighboring pixel, the pixel quality is negatively correlated with a difference between a pixel value of the pixel and a pixel median value, and the fusion coefficient is positively correlated with the contrast and the pixel quality; and fusing the at least two initial ultrasound images of the target tissue according to the obtained fusion coefficient maps corresponding to the at least two initial ultrasound images to obtain the fused ultrasound image of the target tissue.

6. The method of claim 5, wherein fusing the at least two initial ultrasound images of the target tissue according to the obtained fusion coefficient maps corresponding to the at least two initial ultrasound images comprises:

calculating a sum of products of pixel values at a position of a pixel in the at least two initial ultrasound images and corresponding fusion coefficients to obtain a pixel value at the position of pixel in the fused ultrasound image.

7. The method of claim 5, wherein fusing the at least two initial ultrasound images of the target tissue according to the obtained fusion coefficient maps corresponding to the at least two initial ultrasound images comprises:

performing multi-scale decomposition on each initial ultrasound image and its corresponding fusion coefficient map to obtain ultrasound sub-images and their corresponding fusion coefficient sub-maps at multiple scales;

fusing all ultrasound sub-images at each scale according to their corresponding fusion coefficient sub-maps to obtain fused ultrasound sub-images at the multiple scales; and reconstructing the fused ultrasound sub-images at the multiple scales to obtain the fused ultrasound image.

8. The method of claim 7, wherein performing the multi-scale decomposition on each initial ultrasound image and its corresponding fusion coefficient map comprises:

performing Laplacian pyramid decomposition on each initial ultrasound image; and performing Gaussian pyramid decomposition on the fusion coefficient map corresponding to each initial ultrasound image.

9. The method of claim 4, wherein fusing the at least two initial ultrasound images according to the image characteristic to obtain the fused ultrasound image of the target tissue comprises:

performing decomposition on each initial ultrasound image using a same image decomposition method, to obtain multiple characteristic sub-images of the at least two initial ultrasound images; and fusing the obtained multiple characteristic sub-images to obtain the fused ultrasound image of the target tissue.

10. The method of claim 9, wherein performing the decomposition on each initial ultrasound image using the same image decomposition method, to obtain the multiple characteristic sub-images of the at least two initial ultrasound images comprises:

performing singular value decomposition on each initial ultrasound image to obtain a left singular matrix, a singular value matrix, and a right singular matrix of each of the at least two initial ultrasound images, wherein the singular value matrix comprises singular values of the initial ultrasound image, the left singular matrix comprises a left singular vector corresponding to a singular value in the singular value matrix, and the right singular matrix comprises a right singular vector corresponding to a singular value in the singular value matrix; and determining a characteristic sub-image corresponding to the singular value according to the singular value and its corresponding left singular vector and right singular vector to obtain the multiple characteristic sub-images of the at least two initial ultrasound images, wherein an amplitude or energy of the singular value is greater than a preset threshold.

11. The method of claim 10, wherein fusing the obtained multiple characteristic sub-images to obtain the fused ultrasound image of the target tissue comprises:

determining a fusion coefficient of the characteristic sub-image corresponding to the singular value according to the amplitude or energy of the singular value; and performing weighted fusion on the obtained multiple characteristic sub-images according to the fusion coefficient to obtain the fused ultrasound image of the target tissue.

12. The method of claim 9, wherein performing the decomposition on each initial ultrasound image using the same image decomposition method, to obtain the multiple characteristic sub-images of the at least two initial ultrasound images comprises:

performing wavelet decomposition on each initial ultrasound image using a same wavelet base and decomposition level, and determining a characteristic sub-image for representing an overall structural feature, a characteristic sub-image for representing a local detail feature in a horizontal direction, a characteristic sub-image for representing a local detail feature in a vertical direction, and a characteristic sub-image for representing a local detail feature in a diagonal direction at each decomposition level, to obtain the multiple character-istic sub-images of the at least two initial ultrasound images.

13. The method of claim 12, wherein fusing the obtained multiple characteristic sub-images to obtain the fused ultra-sound image of the target tissue comprises:

fusing, according to fusion coefficients, characteristic sub-images located at a same decomposition level and used for representing a same type of feature, to obtain a fused characteristic sub-image at each decomposition level, wherein the fusion coefficient is a preset fusion coefficient or is determined according to an amplitude of the characteristic sub-image; and performing inverse wavelet transform on fused charac-teristic sub-images at all decomposition levels to deter-mine the fused ultrasound image of the target tissue.

14. The method of claim 9, wherein performing the decomposition on each initial ultrasound image using the same image decomposition method, to obtain the multiple characteristic sub-images of the at least two initial ultra-sound images comprises:

decomposing each initial ultrasound image using a same empirical mode decomposition method to obtain a preset quantity of detail characteristic sub-images for representing image detail information at different scales and one structural characteristic sub-image con-taining image brightness information, so as to obtain the multiple characteristic sub-images of the at least two initial ultrasound images, wherein the detail char-acteristic sub-image is determined according to an intrinsic mode function component, and the structural characteristic sub-image is determined according to a decomposition residual.

15. The method of claim 14, wherein fusing the obtained multiple characteristic sub-images to obtain the fused ultra-sound image of the target tissue comprises:

fusing the detail characteristic sub-images at each scale to obtain a fused detail characteristic sub-image at the scale, so as to obtain a preset quantity of fused detail characteristic sub-images;

fusing the structural characteristic sub-images to obtain one fused structural characteristic sub-image; and performing reconstruction according to the preset quan-tity of fused detail characteristic sub-images and the one fused structural characteristic sub-image, to obtain the fused ultrasound image of the target tissue.

16. The method of claim 1, further comprising:

respectively generating ultrasound images of the target tissue corresponding to the at least two different ultra-sound beamforming methods according to the at least two image data frames; and displaying the ultrasound images of the target tissue corresponding to the at least two different ultrasound beamforming methods.

17. The method of claim 1, wherein the at least two different ultrasound beamforming methods comprise at least two of a delay-and-sum beamforming method, a minimum variance beamforming method, a coherence factor beam-forming method, an incoherent beamforming method and a frequency domain beamforming method.

18. An ultrasound beamforming method, comprising:

obtaining channel data from echoes returned from a target tissue;

obtaining a type of the target tissue and determining the at least two different ultrasound beamforming methods according to the type of the target tissue and a pre-established mapping relationship between a type of tissue and an ultrasound beamforming method; and performing at least two beamforming processes on the channel data using the at least two different ultrasound beamforming methods to obtain at least two groups of beamformed data of the target tissue corresponding to the at least two different ultrasound beamforming meth-ods, wherein the at least two different ultrasound beam-forming methods are different in at least one of a principle, a step, and a parameter; fusing the at least two groups of beamformed data corresponding to the at least two different ultrasound beamforming methods to obtain fused beamformed data of the target tissue; and generating an ultrasound image of the target tissue according to the fused beamformed data.

19. An ultrasound imaging device, comprising:

an ultrasonic probe;

a transmitter circuit configured to control the ultrasonic probe to transmit an ultrasound wave to a target tissue;

a receiver circuit configured to control the ultrasonic probe to receive echoes of the transmitted ultrasound wave to obtain channel data of the target tissue;

a display configured to output visual information; and a processor configured to perform:

obtaining the channel data of the target tissue;

obtaining a type of the target tissue and determining at least two different ultrasound beamforming methods according to the type of the target tissue and a pre-established mapping relationship between a type of tissue and an ultrasound beamforming method; and performing at least two beamforming processes on the channel data using the at least two different ultra-sound beamforming methods to obtain at least two image data frames of the target tissue corresponding to the at least two different ultrasound beamforming methods, wherein, the at least two beamforming processes are performed on same channel data and each of the at least two different ultrasound beam-forming methods correspondingly obtains one image data frame, and the at least two different ultrasound beamforming methods are different in at least one of a principle, a step, and a parameter.

* * * * *